US 6,622,561 B2

(12) United States Patent
Lam et al.

(10) Patent No.: US 6,622,561 B2
(45) Date of Patent: Sep. 23, 2003

(54) TUBULAR MEMBER FLAW DETECTION

(75) Inventors: Clive Chemo Lam, Tomball, TX (US); Joseph Gregory Kemper, Houston, TX (US); Antonio Manocchio, Houston, TX (US)

(73) Assignee: Varco I/P, Inc., Houston, TX (US)

( * ) Notice: Subject to any disclaimer, the term of this patent is extended or adjusted under 35 U.S.C. 154(b) by 72 days.

(21) Appl. No.: 10/052,237

(22) Filed: Jan. 18, 2002

(65) Prior Publication Data
US 2003/0033881 A1 Feb. 20, 2003

Related U.S. Application Data

(63) Continuation-in-part of application No. 09/930,117, filed on Aug. 14, 2001, now Pat. No. 6,578,422.

(51) Int. Cl.[7] .............................................. G01N 29/10
(52) U.S. Cl. ............................ 73/622; 73/627; 73/620
(58) Field of Search ........................ 73/602, 622, 623, 73/627, 620

(56) References Cited

U.S. PATENT DOCUMENTS

| | | |
|---|---|---|
| 3,437,917 A | 4/1969 | Gunkel et al. |
| 3,455,150 A | 7/1969 | Wood |
| 3,489,679 A | 1/1970 | Davidson et al. |
| 3,741,003 A | 6/1973 | Gunkel ........................ 73/67.7 |
| 3,759,090 A | 9/1973 | McFaul et al. ............... 73/67.6 |
| 3,766,775 A | 10/1973 | Gunkel ..................... 73/67.8 S |
| 3,868,847 A | 3/1975 | Gunkel ..................... 73/67.8 S |
| 3,894,425 A | 7/1975 | Winters et al. ................. 73/640 |
| 3,918,294 A | 11/1975 | Makino et al. ............... 73/67.2 |
| 3,942,358 A | 3/1976 | Pies ............................ 73/67.7 |
| 3,949,227 A | 4/1976 | Gambini et al. ......... 250/358 P |
| 3,969,926 A | 7/1976 | Walker et al. ............ 73/67.8 S |
| 3,974,684 A | 8/1976 | Roule et al. ............ 73/71.5 US |

(List continued on next page.)

FOREIGN PATENT DOCUMENTS

| | | | |
|---|---|---|---|
| GB | 2124379 A | 2/1984 | |
| GB | 2280507 A | 2/1995 | |
| JP | 57070455 A | * 4/1982 | .......... G01N/29/04 |
| JP | 62100658 A | * 5/1987 | .......... G01N/29/04 |
| JP | 07280776 A | * 10/1995 | .......... G01N/29/10 |
| JP | 09108924 A | * 4/1997 | ............. B23C/7/02 |
| SU | 480-973 | 8/1975 | |

OTHER PUBLICATIONS

Ultrasonic NDT Instruments and Systems, Matec Instrument Companies, 2001.
CFER, Center For Frontier Engineering Research, Annual Report 1986–87, p. 9.
Abstract for Russia SU 480 975.

*Primary Examiner*—Helen Kwok
*Assistant Examiner*—Rose M. Miller
(74) *Attorney, Agent, or Firm*—Guy McClung

(57) ABSTRACT

A method for ultrasonically inspecting a tubular member which has a first surface spaced-apart from a second surface by a thickness of the tubular member, and two spaced-apart ends the method including transmitting sonic beams to the tubular member with transducer apparatus which are reflected from the first surface and from the second surface, the transducer apparatus controlled by control apparatus, while to inspect the first surface for first surface defects, moving the transducer apparatus adjacent sensing apparatus which signals the control apparatus to cease processing of signals related to inspection of the second surface, and, the transducer apparatus continuing to transmit sonic beams for the inspection of the first surface, and completing inspection of substantially all of the second surface for second surface defects while continuing to inspect the first surface.

25 Claims, 12 Drawing Sheets

U.S. PATENT DOCUMENTS

| | | | |
|---|---|---|---|
| 3,975,948 A | 8/1976 | Makino et al. | 73/67.2 |
| 3,981,184 A | 9/1976 | Matay | 73/67.8 S |
| 3,985,022 A | 10/1976 | Dileo et al. | 73/67.8 R |
| 3,986,389 A | 10/1976 | Mesina et al. | 73/67.9 |
| 3,991,607 A | 11/1976 | Niklas | 73/67.7 |
| 3,992,925 A | 11/1976 | Perilhou | 73/67.7 |
| 3,994,154 A | 11/1976 | Niklas et al. | 73/67.8 R |
| 3,996,792 A | 12/1976 | Kubota et al. | 73/67.8 S |
| 3,999,422 A | 12/1976 | Lehmann et al. | 73/67.8 S |
| 4,003,244 A | 1/1977 | O'Brien et al. | 73/67.8 R |
| 4,004,454 A | 1/1977 | Matay | 73/67.8 R |
| 4,010,635 A | 3/1977 | Patsey | 73/67.85 |
| 4,011,750 A | 3/1977 | Robinson | 73/67.7 |
| 4,012,946 A | 3/1977 | Patsey | 73/67.7 |
| 4,026,144 A | 5/1977 | Gericke et al. | 73/67.6 |
| 4,062,227 A | 12/1977 | Heyman | 73/630 |
| 4,078,427 A | 3/1978 | Yoshida et al. | 73/194 A |
| 4,248,092 A | 2/1981 | Vasile et al. | 73/643 |
| 4,361,044 A | 11/1982 | Kupperman et al. | 73/623 |
| 4,404,853 A | 9/1983 | Livingston | 73/522 |
| 4,471,657 A | 9/1984 | Voris et al. | 73/597 |
| 4,475,399 A | 10/1984 | Livingston | 73/622 |
| 4,487,072 A | 12/1984 | Livingston | 73/622 |
| 4,541,064 A | 9/1985 | Livingston | 364/552 |
| 4,569,229 A | 2/1986 | Detalleau | 73/597 |
| 4,665,734 A * | 5/1987 | Joet | 73/622 |
| 4,700,572 A | 10/1987 | Senba et al. | 73/622 |
| 4,700,576 A | 10/1987 | Grare et al. | 73/761 |
| 4,718,277 A | 1/1988 | Glascock | 73/622 |
| 4,735,269 A | 4/1988 | Park et al. | 175/46 |
| 4,846,001 A | 7/1989 | Kibblewhite | 73/761 |
| 4,870,866 A | 10/1989 | Slack | 73/599 |
| 5,007,291 A | 4/1991 | Walters et al. | 73/640 |
| 5,400,645 A | 3/1995 | Kunze et al. | 73/40.5 A |
| 5,419,334 A | 5/1995 | Miyagawa | 128/662.06 |
| 5,460,046 A | 10/1995 | Maltby et al. | 73/623 |
| 5,914,596 A | 6/1999 | Weinbaum | 324/228 |
| 6,230,568 B1 | 5/2001 | Winston et al. | 73/601 |
| 6,230,799 B1 | 5/2001 | Slaughter et al. | 166/249 |
| 6,231,510 B1 | 5/2001 | Negrin et al. | 600/443 |
| 6,231,511 B1 | 5/2001 | Bae | 600/447 |
| 6,231,513 B1 | 5/2001 | Daum et al. | 600/458 |
| 6,398,731 B1 | 6/2002 | Mumm et al. | 600/437 |
| 6,474,165 B1 | 11/2002 | Harper et al. | 73/623 |

* cited by examiner

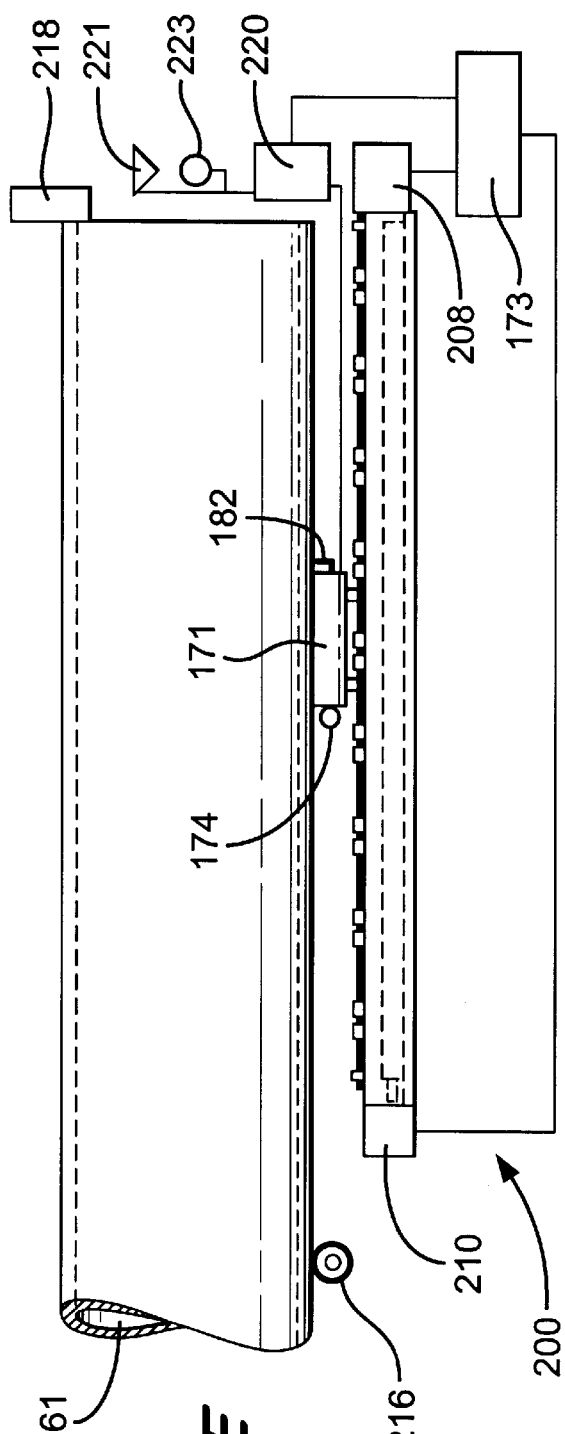
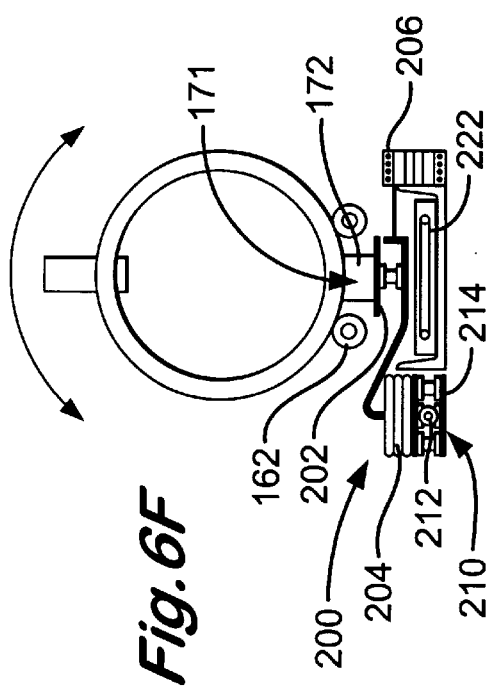
Fig. 6E
Fig. 6F

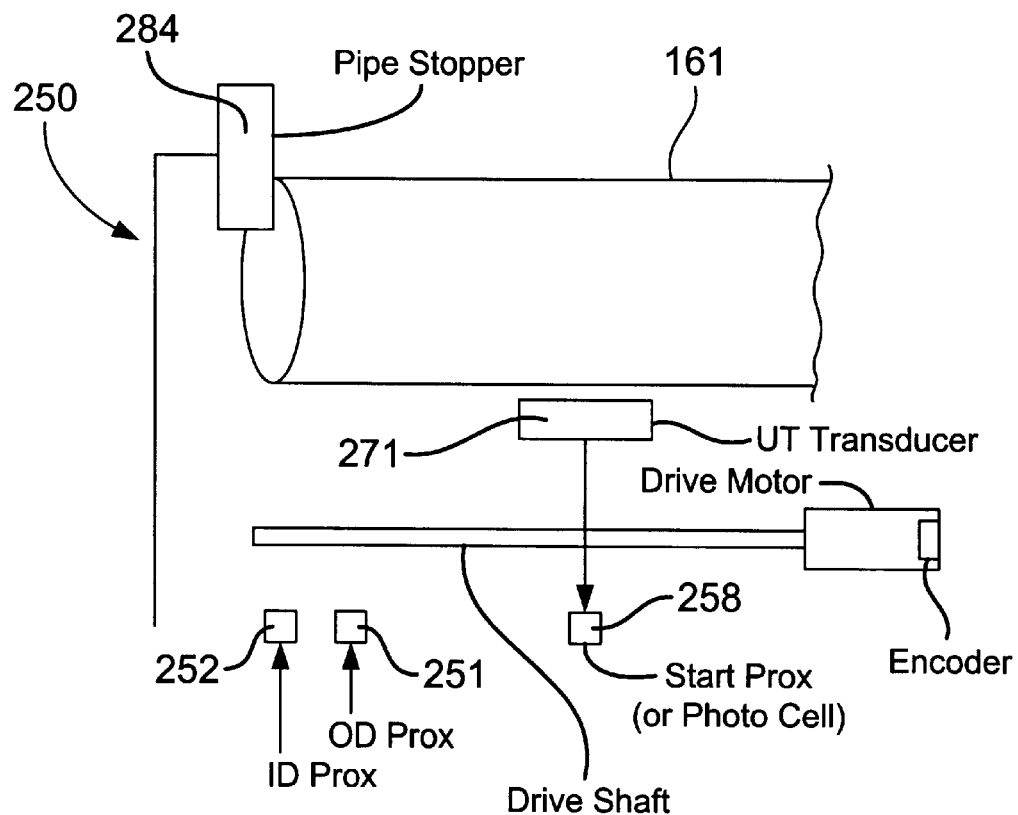
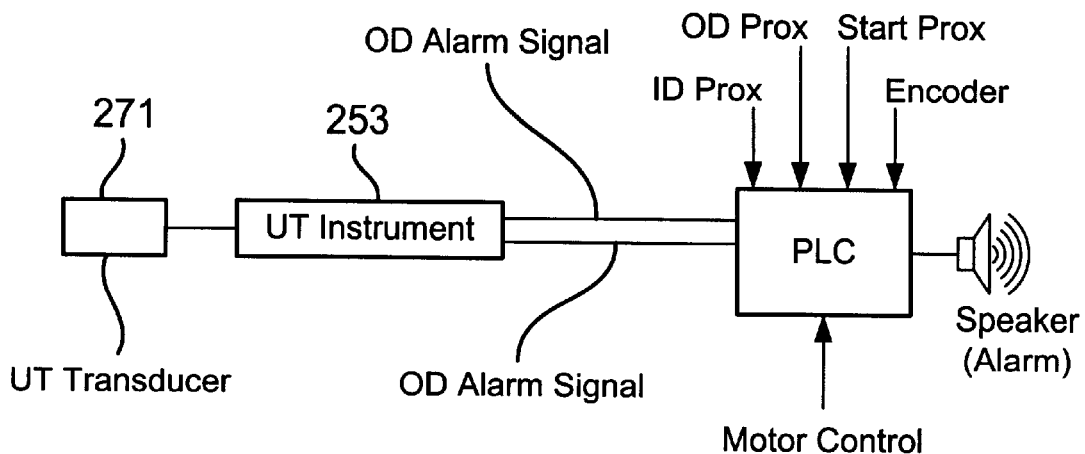

TUBULAR MEMBER FLAW DETECTION

RELATED APPLICATION

This is a continuation-in-part of U.S. Ser. No. 09/930,117 filed Aug. 14, 2001, incorporated fully herein for all purposes now U.S. Pat. No. 6,578,422.

BACKGROUND OF THE INVENTION

1. Field of the Invention

The invention is directed to: ultrasonic systems and methods for detecting flaws in tubular members; in certain particular aspects, to such systems and methods that are automatic and which accurately detect flaws near or at the ends of a tubular member such as pipe, tubing, casing, or other oil field tubulars; and, in certain aspects, to systems and methods for detecting defects in welds in, on, or between tubular members.

2. Description of Related Art

Flaws and defects in tubular members can result in the failure of the tubulars. Replacement or repair of a defective tubular can be time-consuming and expensive. In the oil and gas industries, tubular members used in drilling and other oil field operations are examined before use to detect and locate defects. Often a defect can be removed and the tubular used for its intended purpose. In other cases, the defect cannot be fixed and the tubular is rejected. Whether the tubular member can be used is based on characteristics of a defect, e.g. size, shape, location and orientation.

In some cases, defects located on a surface (interior or exterior) of a tubular can be visually characterized and examined to determine whether removal of the defect is necessary and possible—and whether removal is feasible by grinding or other means; but often such visual examination of a defect is not accurate or is not possible.

Certain prior art ultrasonic inspection devices have used sonic beams to locate defects in tubular members. In certain systems the apparatus employed uses a piezoelectric crystal or crystals, each of which produces ultrasonic vibrations in response to the application of a voltage. Such systems often use a method in which a crystal is held in a position relative to the pipe surface to transmit a short duration sonic wave pulse of beamed energy into the wall of the pipe at an angle such that a flaw or discontinuity in the pipe causes the waves to be reflected back and produce a voltage response in the crystal, which is then de-energized immediately following the pulsed emission of a sonic wave so that reflected waves can be received during the de-energized periods to produce a corresponding electrical signal which may be analyzed for determining the nature and location of flaws. For example, U.S. Pat. No. 4,217,782 describes an ultrasonic inspection device for inspecting tubular members for the oil and gas drilling industries that employs two pairs of line-focused transducers that transmit sonic beams having a rectangular beam cross-section of about ¾ inch in length. A first pair of the transducers transmits sonic beams longitudinally into the member to detect transverse defects. The second pair transmits sonic beams transversely into the member to detect longitudinal defects. The transducers in each pair transmit sonic beams in opposite directions. Two additional transducers monitor the wall thickness of the tubular member. Sonic beams transmitted longitudinally and transversely are used for the inspection of tubular members since defects are visible to only one or the other. Some flaws and defects are invisible to both longitudinally and transversely transmitted sonic beams. In certain prior art systems, the ultrasonic inspection device of U.S. Pat. No. 4,217,782 has been modified to include four spot-focused transducers that transmit sonic beams having a circular beam cross-section obliquely through a tubular member and a pair of transducers that transmit in opposite directions has been used to detect defects in tubular members as described in U.S. Pat. No. 3,289,468 since a given defect may be invisible to a transducer looking at it from one direction and visible to a transducer looking at it from the opposite direction.

In order to characterize a defect for size, shape, and orientation sonic beams are, in certain prior art systems, transmitted from several different directions followed by the receiving of beams reflected from the defect. As described in U.S. Pat. No. 3,332,278, reflected beams from one transducer have been received by several transducers to detect some of the defects.

U.S. Pat. No. 4,718,277 discloses an ultrasonic inspection device having an array of opposing transducers that longitudinally, transversely, and obliquely transmit sonic beams through tubular members having a range of diameters such that refracted beams meet on the inner surface of the members. Alternate halves of the array of transducers transmit and receive sonic beams reflected from defects in the tubular members using both the pulse-echo and pitch-catch methods.

U.S. Pat. No. 5,007,291 discloses ultrasonic inspection apparatus with centering means for tubular members that has pipe inspection apparatus with transducers for transmitting pulsed beams of ultrasonic energy longitudinally, transversely and obliquely into the wall of the pipe for detection of flaws. The apparatus includes a motor driven chuck for rotating the transducers about the a pipe and a motor driven roller for axial movement of the pipe whereby the transducers move in a helical scanning path. A control system maintains the axes of the pipe and circle array of transducers in coincidence and with hydraulic controls maintains each transducer at fixed distance to the pipe for sonicly coupling thereto by a flowing liquid whereby a shear wave is generated by each beam in the tubular wall. The transducers comprise multiple pairs, the members of which are diametrically opposed and transmit in opposite directions, for transmitting longitudinally at angles of 12 degrees, 27 degrees and 42 degrees to the pipe axis both clockwise and counterclockwise with one transducer of each pair disposed to transmit forward and the other reverse. For longitudinal flaws, one transducer of a pair transmits transverse clockwise and the other transverse counterclockwise. All transducers which transmit in a given direction are arrayed in the axial direction of the pipe. Pulsers simultaneously and repetitively energize and de-energize all forward transmitting transducers and after each such transmission pulsers simultaneously and repetitively energize and de-energize all reverse transducers. Reflection signals of predetermined strength are recorded and activate an alarm. A compressional wave transducer for determining wall thickness is included.

U.S. Pat. No. 5,313,837 discloses an ultrasonic thickness gage for pipe, which in certain aspects is a compact ultrasonic tester involving rotating sensors. A processor rotates with the sensors so that the output signal of the processor goes through slip rings, rather than to output signal of the sensors. A spraying system is incorporated in conjunction with rollers. The rollers take the applied spray on the pipe surface and paint a film on the outer pipe surface to allow a good contact for meaningful results. A floating shoe is provided for holding each sensor against the pipe wall. The sensors are biased into contact with the pipe surface and the machine can handle different diameters of pipe. By controlling the pipe speed of advance and the rotational speed of the sensors, a large percent coverage of the pipe wall is assured. The machine is compact and can be installed behind existing electromagnetic/gamma testers without major modifications to pipe-testing facilities.

U.S. Pat. No. 5,585,565 discloses a method for the ultrasonic inspection of pipe and tubing and a transducer which has an elastic membrane used to form a reservoir of ultrasonic fluid coupled to ultrasonic transducers with the membrane conforming to the surface of the tubing being inspected. Guide wheels maintain the membrane out-of-contact with the tubing during relative rotational movement of the assembly and tubing during inspection. Water is introduced between the membrane and the tubing to provide ultrasonic coupling of the tubing to the transducers through the fluid of the reservoir. Each of the patents mentioned above is incorporated fully herein in its entirety for al purposes.

Known automated ultrasonic systems for detecting flaws and defects in tubulars have been unable to adequately, accurately, and correctly detect inner surface defects relatively near the ends of the tubular member, e.g., within two feet or within eighteen inches of the ends up to the end boundary surface. For example, about eighteen to twenty four inches of the length of a thirty foot casing, ten and three-fourths inches in diameter, is often not accurately examined by certain automated prior art systems. The ends of such tubulars are often examined manually with portable electromagnetic or ultrasonic testing equipment in a time-consuming process. In various prior art systems the signals from the ends of the tubulars are not accurately distinguished from signals reflected from defects near the ends of the tubulars. This inability to distinguish and differentiate these signals renders these systems and methods inadequate for inner surface defect detection near the tubulars' ends.

There has been a need for an ultrasonic inspection device that is capable of correctly and efficiently detecting and characterizing flaws and defects in tubular members and for such systems and methods that can do this for inner surface defects near or at the ends of the tubulars. There has long been a need for systems and methods for detecting defects in welds in, on, or between tubulars, e.g., but not limited to, the examination of girth welds of tool joints.

SUMMARY OF THE INVENTION

The present invention, in certain aspects, discloses a method for ultrasonically inspecting a tubular member, the tubular member having a first surface, a second surface, the first surface spaced apart from the second surface by a thickness of the tubular member, and two spaced-apart ends including a first end of the tubular member, the method including transmitting sonic beams to the tubular member with transducer apparatus such that sonic beams are reflected from the first surface of the tubular member and from the second surface of the tubular member, the transducer apparatus controlled by control apparatus, while continuing to inspect the first surface of the tubular member for first surface defects, moving the transducer apparatus adjacent sensing apparatus which signals the control apparatus to cease processing of transducer apparatus signals related to inspection of the second surface, and, the transducer apparatus continuing to transmit sonic beams for the inspection of the first surface of the tubular member, and completing inspection of the second surface of the tubular member for second surface defects while continuing to inspect the first surface of the tubular member for first surface defects.

The present invention discloses, in certain aspects, an ultrasonic inspection device useful for inspecting a tubular member including transducer apparatus for transmitting sonic beams and for receiving reflected beams thereof from inner and outer surfaces of the tubular member, and from defects of the tubular member, the reflected beams including beams reflected from an outer surface of the tubular member and from an inner surface of the tubular member, and from a defect of the tubular member, and apparatus for differentiating the reflected beams, apparatus for producing signals corresponding to information about the reflected beams, including a defect signal having information about the defect, and an end signal from proximity switch apparatus positioned with respect to an end of the tubular member, and apparatus for continuing inspection of one surface of the tubular member following cessation of inspection of the other surface of the tubular member.

The present invention, in certain embodiments, discloses a system for detecting defects in tubular members which is capable of examining almost all of the entire length of the tubular; and, in certain aspects, which can accurately detect flaws including inner surface defects in substantially all of a tubular's length and near or at its ends. In certain aspects this is accomplished with a system that nullifies, cancels, or ignores information from a signal reflected from a tubular end (or signals)—i.e. other than a signal or signals related to inner surface defects—transmitted to and reflected from the tubular. In many instances a signal reflected from a tubular end is misinterpreted as, is not easily distinguishable from or is indistinguishable from a signal reflected from an inner surface defect near a tubular end and such a signal often cannot be accurately analyzed to determine whether there is a defect near the tubular end. A misinterpretation of such a signal can also result in a false indication of an inner surface defect.

In certain embodiments according to the present invention, signal information related to a signal reflected from the end of the tubular is used by an analyzing apparatus to determine the distance from ultrasonic transducers to the end of the tubular toward which the transducers are moving, but not for outer surface (outer diameter or "O.D.") flaw detection; and, at the same time, the system does send and receive signals for the examination of the inner surface (inner diameter or "I.D.") of the tubular member relatively near its end. By knowing the distance from the ultrasonic transducer(s) to the end of the tubular member, once the tubular's outer surface has been examined, signals other than those related to examination of the inner surface and determining the distance to the tubular end can be ignored.

In certain aspects a system according to the present invention employs a transducer mount or "shoe" that has a plurality (two, three, four, five or more) of ultrasonic transducers each of which can emit a beam that is reflected back to a receiving ("listening") transducer. In one aspect the reflected beams pass through a single beam passage area of the shoe for receipt by one of the transducers which is not in a beam-emitting mode (a "listening" mode).

In one embodiment a shoe according to the present invention has a waveguide support for transducers that is made of Lucite (trademark) plastic or of similar plastic (or of low loss ultrasonic material). Multiple—e.g., two, three, four or five—transducers are mounted relatively close to each other. Each transducer is mounted at a prescribed angle so that, in certain aspects, all reflected beams pass through the single beam passage area of the waveguide and are directed back to one of the transducers. In certain aspects such a system may also have one, two or more transducers located apart from the plastic waveguide support for examining the wall thickness of the tubular being studied. Alternatively, the wall-thickness transducer(s) may also be supported by the plastic waveguide support. Optionally a wear member may be mounted adjacent the plastic waveguide support and between it and a tubular for contacting the outer surface of the tubular being examined. The wear member may be a plate with a curved surface corresponding in shape to the curved outer surface of the tubular; it may be a flexible member made of flexible rubber, plastic, or similar material; or it may be an inflatable member such as a bladder or balloon whose contents (e.g. water that acts aa a waveguide) is adjusted to provide a shape that corresponds to the shape of the tubular. Fluid inlet(s) and outlet(s) in the shoe (e.g., but not limited to, in the plastic waveguide support or a mount in which the plastic waveguide support is held) provide fluid to the space between the wear member and the pipe being inspected so that there is no air in this space to impede transmission of the ultrasonic beams. Typical fluids for this include water, silicone, oil, and/or glycol. With a plastic waveguide the angle of refraction of the material is typically about 35.8 degrees. With systems in which the ultrasonic beams are transmitted through water, the angle of refraction is typically about 18.8 degrees.

In certain systems and members according to the present invention a weld on, in or between tubular members is inspected. In one particular embodiment a girth weld (e.g. welding a tool joint to another piece of pipe) is inspected for flaws. In one aspect such a system is automated so that a welded tool joint is rotated adjacent a transducer mount with one, two, three, four, five or more. The transducer mount is moved axially along the length of the joint as it rotates radially so that the entire weld is inspected. Any suitable apparatus for moving the transducer mount adjacent the joint may be used. In one particular aspect the mount is moved continuously until it is adjacent a weld portion; then optionally the mount is moved so that in a position immediately past the weld and the mount is held stationary there while the joint continues to rotate radially adjacent the transducers—thus insuring that the entire weld is inspected and the weld thickness past the weld is examined. Alternatively, the transducer mount is moved along the entire joint length in pre-set incremental steps and the final step is of sufficient temporal duration that the joint continues to rotate through the final step duration so that the wall thickness of the entire weld is inspected. By purposefully moving an ultrasonic transducer apparatus very near or past a weld, the entire weld is subjected to a full ultrasonic beam width.

It is, therefore, an object of at least certain preferred embodiments of the present invention to provide:

New, useful, unique, efficient, nonobvious systems and methods for detecting defects in tubular members such as pipe, casing, tubing, and other tubulars;

Such systems and methods which can effectively and efficiently inspect nearly all of the length of tubular members, etc. relatively near (e.g. within a few millimeters or within an eighth of an inch) the ends thereof for both outer and inner surface defects;

Such systems and methods which accurately distinguish and differentiate an I.D. flaw detection beam reflected from an inner surface defect near a pipe end from a pipe-end-reflected beam;

Such systems and methods which ignore information related to a signal from a pipe-end-reflected beam and/or which nullify or cancel such a beam so that it is not confused with or misinterpreted as a near-pipe-end inner-surface-defect-reflected beam;

New, useful, unique, efficient and nonobvious systems and methods with single beam passage areas for all of a plurality of ultrasonic beams from a plurality of transducers used for tubular defect detection; and New, useful, unique, efficient and nonobvious systems and methods for inspecting welds in, on, or between tubular members and for, in one particular aspect, inspecting entire girth welds of tool joints; and Such systems and methods in which an ultrasonic transducer apparatus is positioned very near or past a weld so that the weld is subjected to the full beam width of an ultrasonic beam, which in one aspect is done by moving the ultrasonic transducer apparatus in step-wise manner adjacent the weld.

Certain embodiments of this invention are not limited to any particular individual feature disclosed here, but include combinations of them distinguished from the prior art in their structures and functions. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention recognizes and addresses the previously-mentioned problems and long-felt needs and provides a solution to those problems and a satisfactory meeting of those needs in its various possible embodiments and equivalents thereof. To one skilled in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of embodiments of the invention briefly summarized above may be had by references to the embodiments which are shown in the drawings which form a part of this specification. These drawings illustrate certain preferred embodiments and are not to be used to improperly limit the scope of the invention which may have other equally effective or legally equivalent embodiments.

FIGS. 6A, 6C and 6E are schematic views of tubular inspection systems according to the present invention. FIG. 6F is an end view of the system of FIG. 6C.

FIGS. 9A and 9B are schematic views of systems according to the present invention.

DESCRIPTION OF EMBODIMENTS PREFERRED AT THE TIME OF FILING FOR THIS PATENT

Figure 1A:
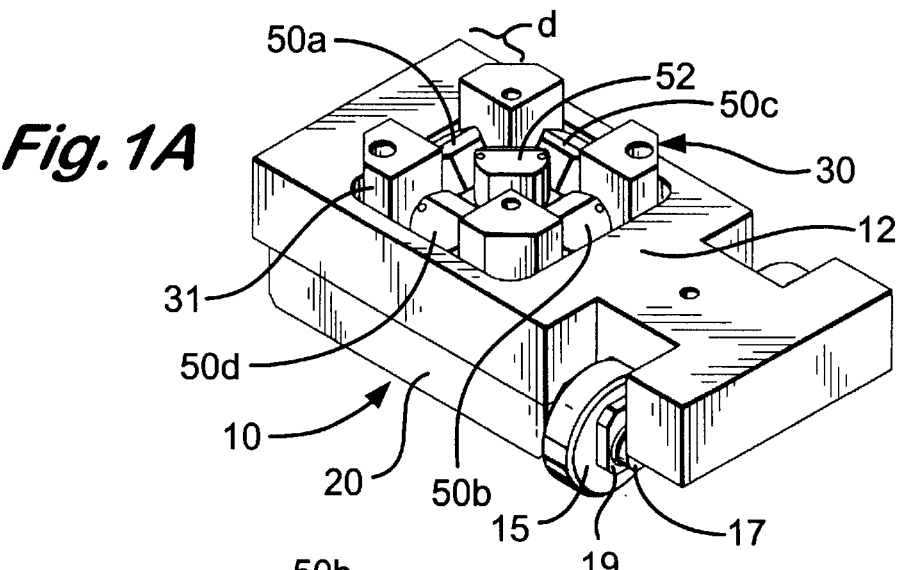
FIGS. 1A and 1B are perspective views of a transducer device according to the present invention.
Figure 1B:
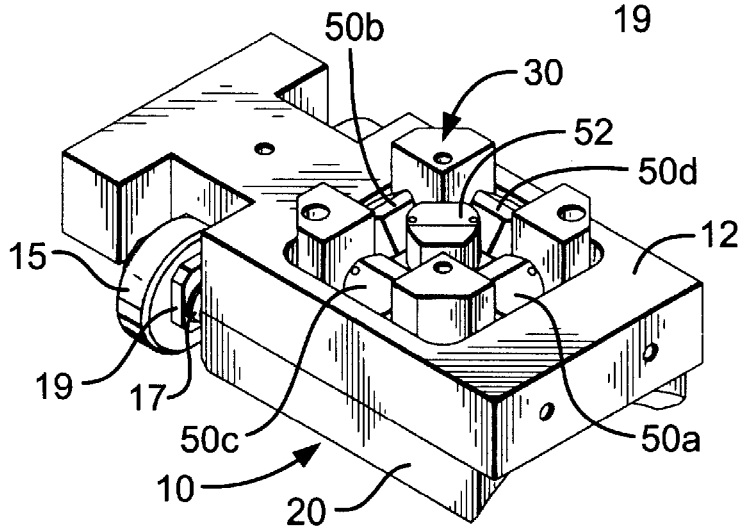
Figure 1C:
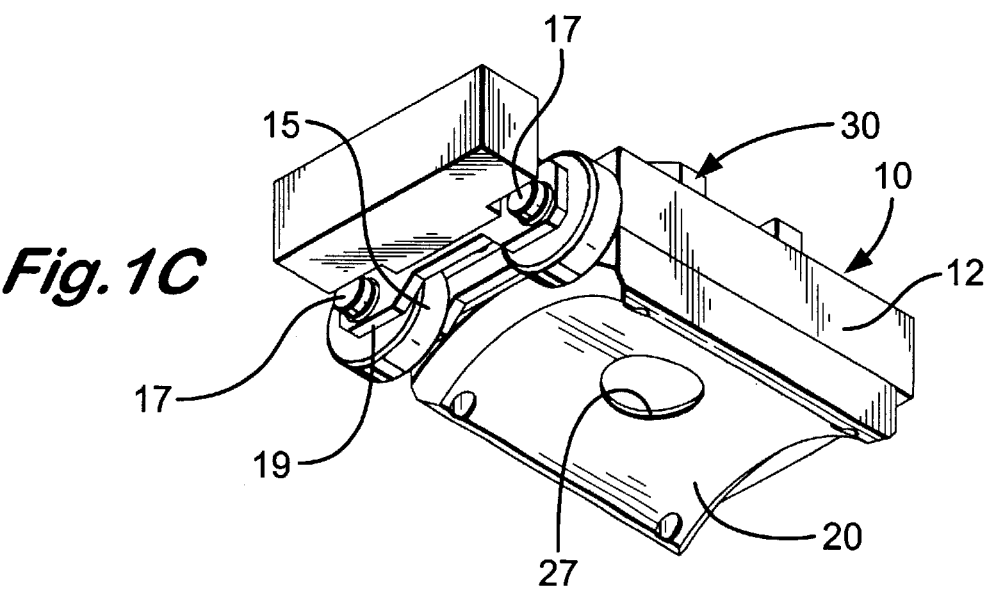
FIG. 1C is a bottom view of the device of FIG. 1A.
Figure 2A:
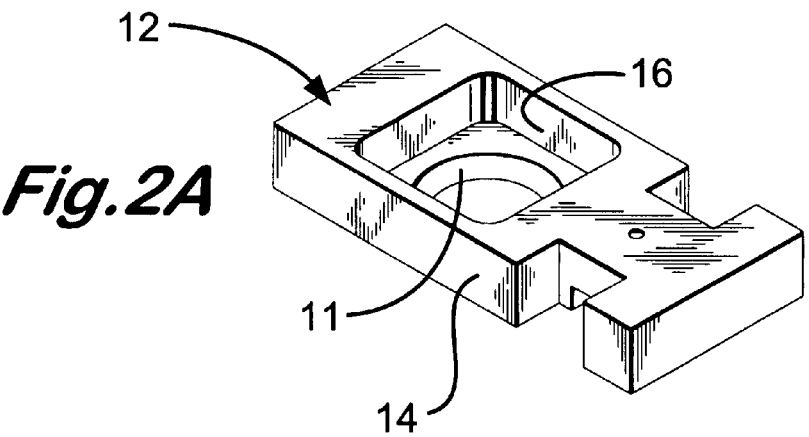
FIG. 2A is top view of a base of the device of FIG. 1A
Figure 2B:
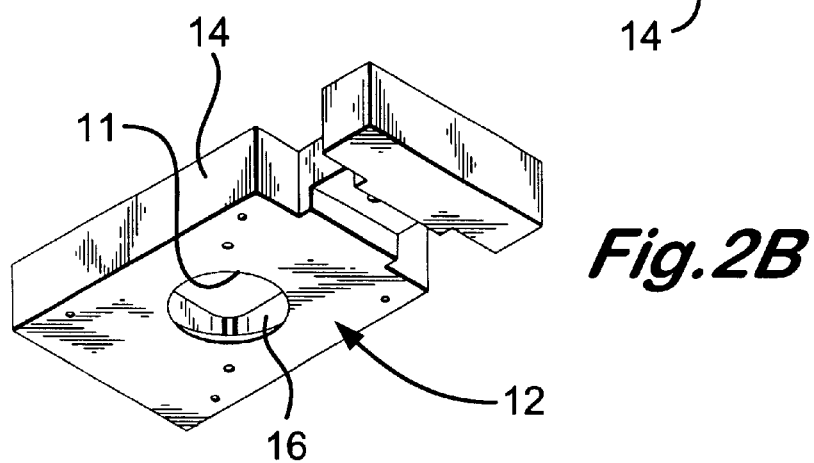
FIG. 2B is a bottom view of the base of FIG. 1A.

FIGS. 1A–1C show a transducer device 10 according to the present invention for use with tubular inspection systems. The device 10 has a base 12; a waveguide support 30; ultrasonic transducers 50a–50d and 52 on the waveguide support 30; and a wearplate 20 secured over one surface of the waveguide member 30.

FIGS. 2A–2E show details of the base 12 of the device 10 of FIG. 1. The base 12 has a body 14 with a recess 16 in which is positioned the waveguide support 30. A bevelled opening 11 receives a correspondingly shaped part of the waveguide support 30 as described below. A roller assembly is secured to the base 12 and has rollers 15 secured to a spacer 19 by bolts 17. These rollers 15 contact the outer surface of a tubular along which the device 10 is moved.

Figure 3A:
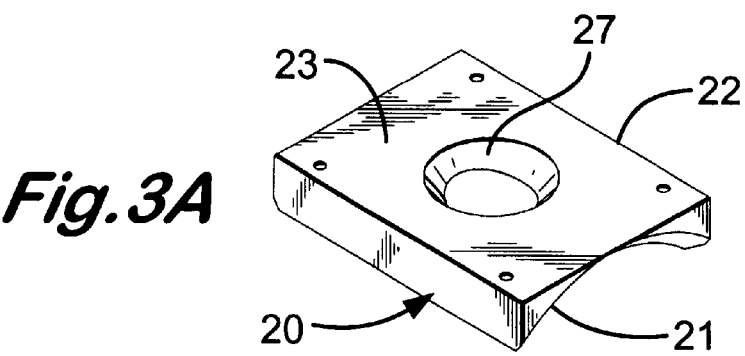
FIG. 3A is a top view of a wearplate of the device of FIG. 1A.
Figure 3B:
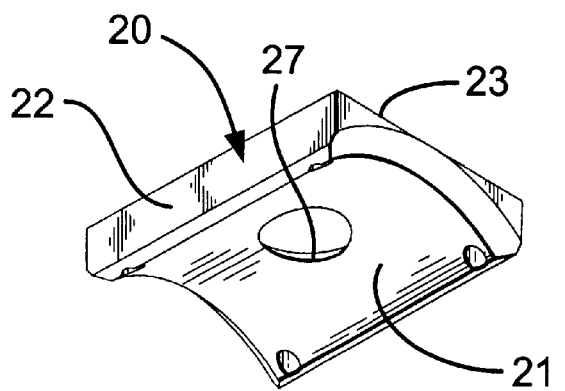
FIG. 3B is bottom view of the wearplate of FIG. 3A.

FIGS. 3A and 3B show the wearplate 20 which has a body 22; front face 21; a beveled opening 27 corresponding in size and location to the opening 11 of the base 12 and through which projects part of the waveguide support 30 as discussed below; and a rear face 23. The front surface 21 of the wearplate 20 is curved to correspond to the curved surface of a tubular being inspected with a system with a device 10, FIG. 1A. The wearplate 20, in certain embodiments, is made of polytetrafluoroethylene.

Figure 4A:
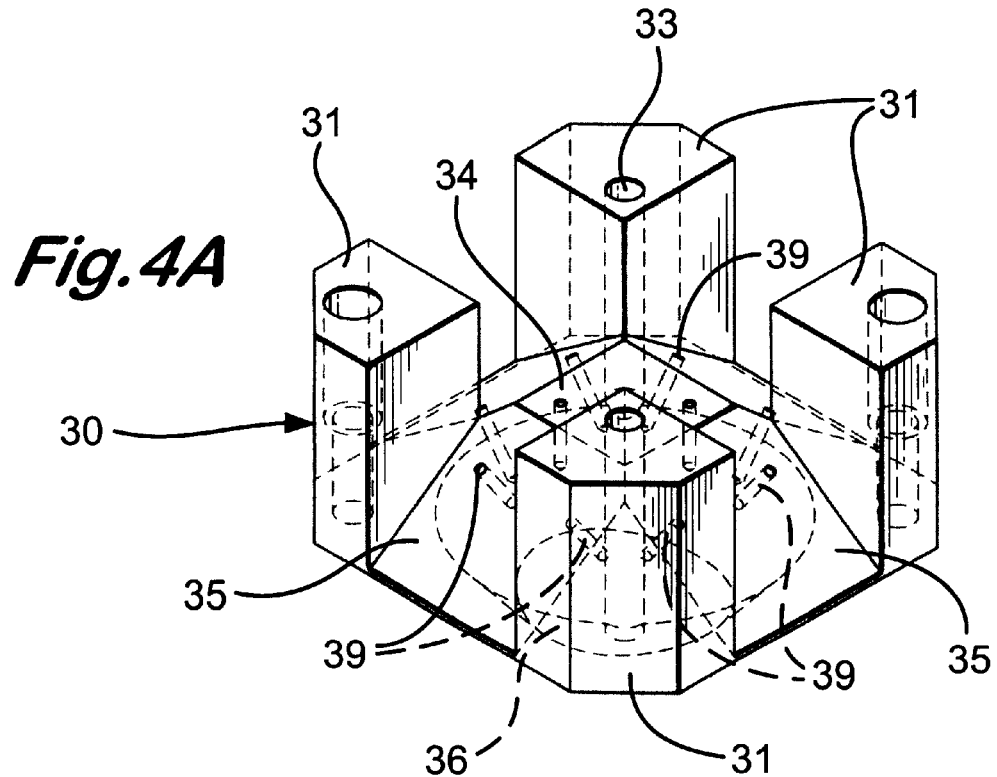
FIG. 4A is top perspective view of a waveguide support of the device of FIG. 1A.
Figure 4B:
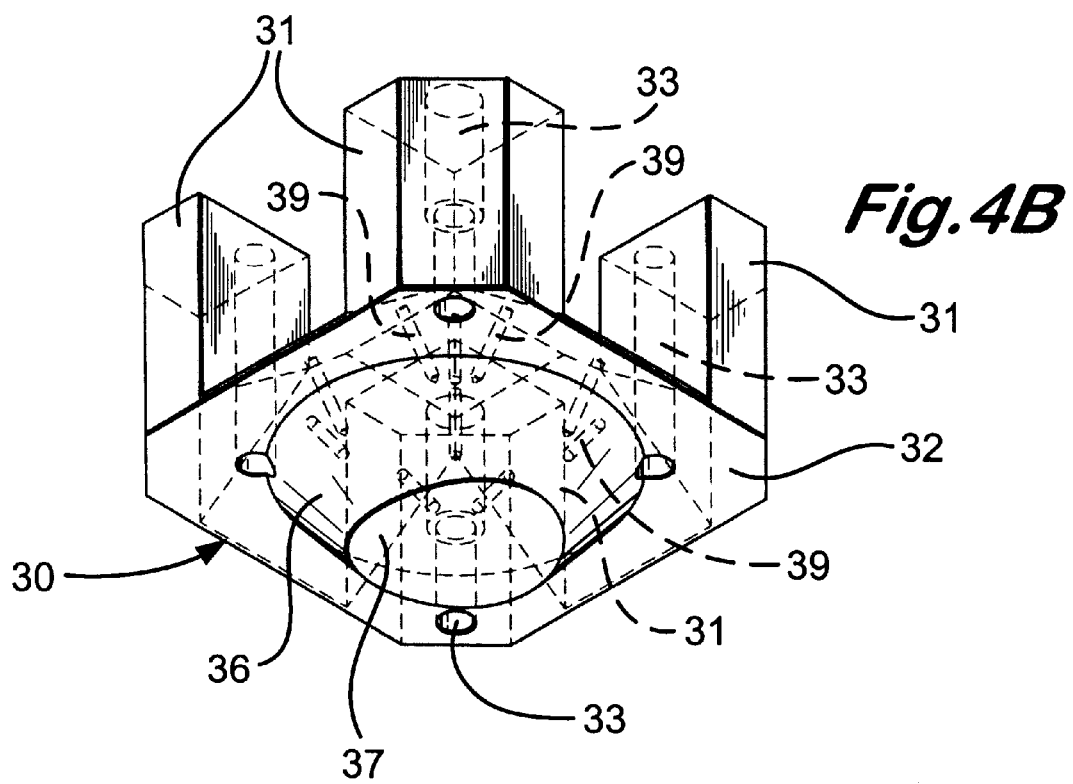
FIG. 4B is a bottom perspective view of the waveguide support of FIG. 4A.

FIGS. 4A and 4B show the waveguide support 30 of the device 10 of FIG. 1A. The transducers shown in FIGS. 1A and 1B have been deleted from FIGS. 4A and 4B. The waveguide support 30 has a body 32 with four spaced-apart pillars 31, each with a hole 33 in it for securing to the base 12. The body 32 has four inclined surfaces 35 to which are secured transducers 50 (see FIG. 1B). The transducers may be coupled with gel or other suitable material and/or held in place with screws or bolts using holes 39. A top surface 34 of the body 32 may be vacant or, optionally, a transducer 52 (see FIG. 1B) may be secured there. A lower member 36 projects down from the body 32. The lower member 36 may have a lower curved portion 37 whose shape corresponds to that of the front surface of the wearplate and to the tubular's outer surface.

The distance "d" in FIG. 1A is the distance from the transducer 50a to the front end of the base 12. In certain aspects the base 12 is moved so that the shoe progresses no further than the distance "d" to the end of the tubular being inspected. In other aspects the shoe is moved so that the opening 27 is beneath the end of the tubular. In other aspects the shoe is moved past the tubular end. In one particular embodiment the distance "d" is about one inch. In certain aspects the opening 27 (and the opening in any version of such a shoe) is about the same size as, is no less than in size, is between 5% to 30% larger in size than, or is about 20% larger in size than the sensitive area of a crystal of an ultrasonic transducer positioned near the opening.

In one embodiment the transducers (e.g., transducers as in FIG. 1A) in a device according to the present invention are so positioned and the waveguide support (e.g., the waveguide support 30) according to the present invention is so sized and configured with its surfaces and dimensions so that all beams—both initial transmitted sonic beams from the transducers and beams reflected from a tubular surface or from a flaw—pass through a single beam passage area (e.g. like the area between the lower member 36 of the waveguide support 30 and through opening 27 of the wearplate 20 and opening 11 of the base 12). In certain aspects the extent of the single beam passage area according to the present invention is slightly larger than the size (e.g., the area) of the sensitive area of the ultrasonic crystal of a transducer. In certain aspects the size of the single beam passage area is between 105% to 125% (or more) of the size of the transducer crystal's sensitive area and in one particular aspect the size of the area is 120% of the size thereof.

FIGS. 5A–5D show a transducer device 100 according to the present invention which has a body 102 to which are secured multiple transducers 106 and an optional transducer 104. Each transducer 106 is mounted in a corresponding recess 107 in the body 102. The transducer 104 is mounted in a recess 108. The body 102 may be made of aluminum, of another suitable metal, of Lucite (trademark) plastic or of similar plastic or material.

A bladder 120 is secured over a recess 114 in the body 102. Optionally a ring (not shown) may be used to hold the bladder in place. Screws through the ring pass into the holes 115 to hold the ring securely to the body 102. Holes 112 provide for the flow of fluid to and from the bladder 120 directly from the holes 112 into the bladder so that the shape of the bladder 120 is adjustable to conform to the shape of a pipe P which is being inspected.

A "single area" 110 between the transducers 106 provides an area through which both transmitted and reflected sonic beam(s) pass.

Figure 6A:
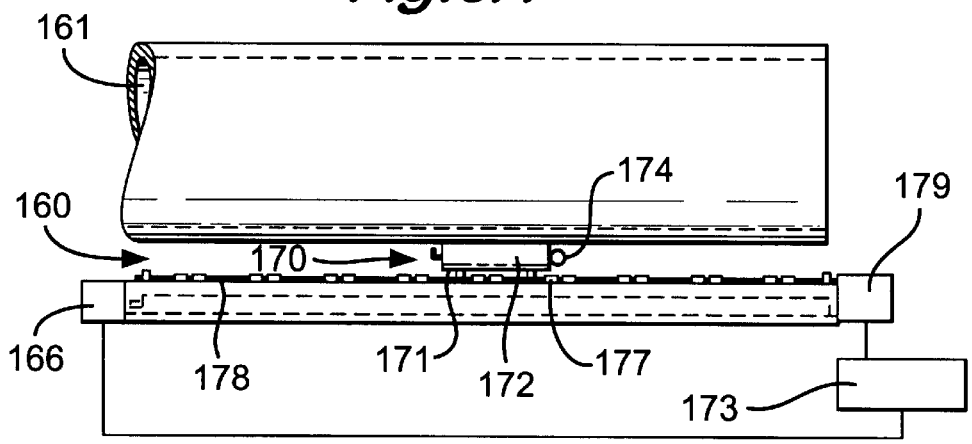
Figure 6B:
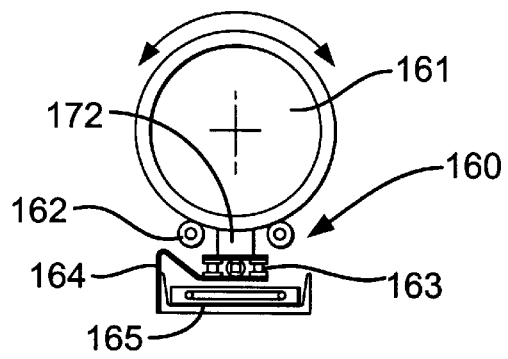
FIG. 6B is an end view of the system of FIG. 6A.
Figure 6D:
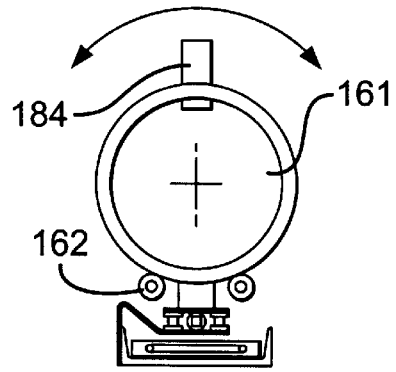
FIG. 6D is an end view of the system of FIG. 6C.
Figure 6C:
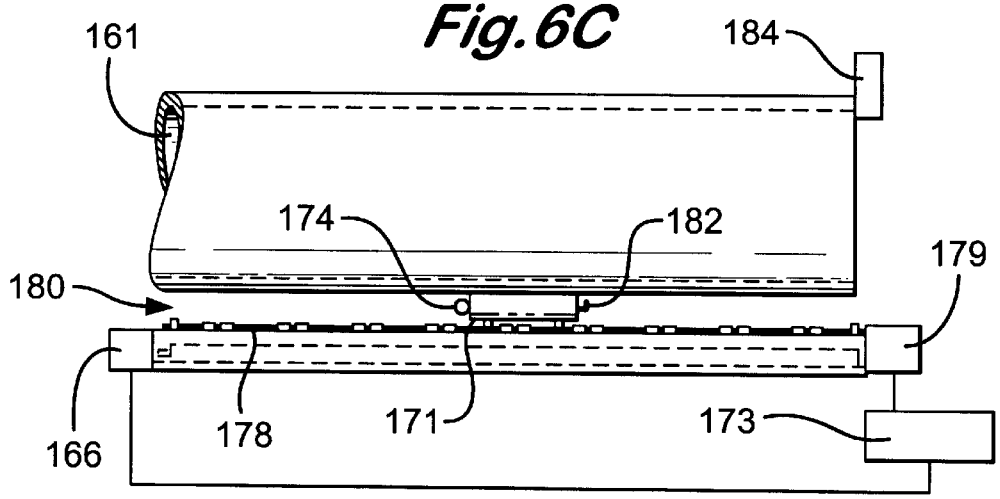

FIGS. 6A, 6C and 6E show schematically systems according to the present invention which use a transducer device according to the present invention to inspect tubulars.

Figure 5A:
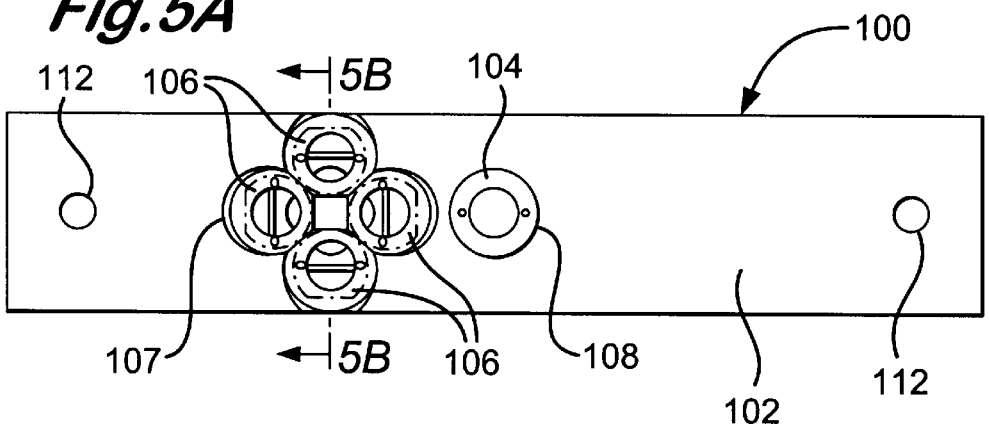
FIG. 5A is top view of a transducer device according to the present invention.
Figure 5B:
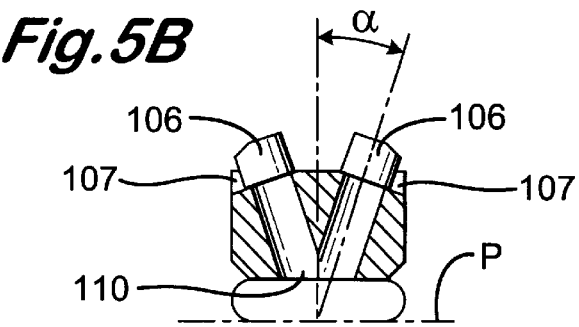
FIG. 5B is a cross-section view along line 5B—5B of FIG. 5A.
Figure 5C:
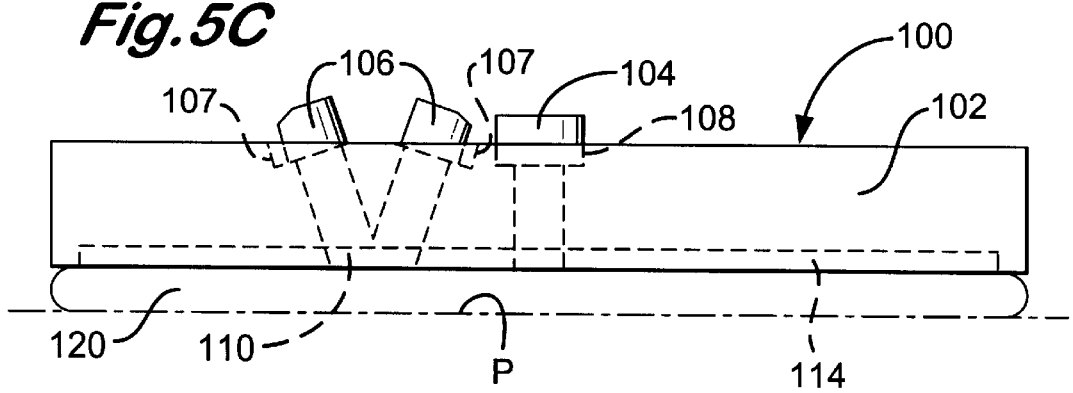
FIG. 5C is a side view along of the device of FIG. 5A.
Figure 5D:
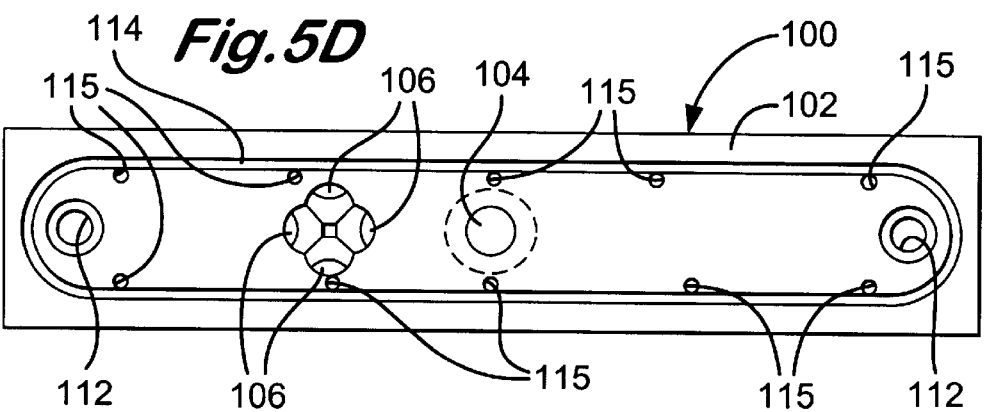
FIG. 5D is a bottom view of the device mount of FIG. 5A.

FIGS. 6A and 6B show a system 160 according to the present invention which has a pipe rotation system 162 for radially rotating a pipe 161 and a sensing system 170 which includes a transducer system 171 with a "shoe" 172 with a plurality of transducers (e.g. but not limited to as in the systems of FIGS. 1A and 5A). Water is supplied to the transducer system 171 by a water supply system 174. A shoe movement system 176 for moving the shoe 172 axially with respect to the pipe 161 includes a mount 177 that is moved on a precision linear motion table 178 by a motor 179. A mounting bracket 164 supports a ball/screw apparatus 163 (optionally with a tracking encoder apparatus 166) which is moved by the motor 179. A water tray 165 is positioned below the shoe 172. A PLC controller 173 controls the motor 179 and, if desired, the rotation system 162.

A system 180 according to the present invention shown in FIGS. 6C and 6D is like the system 160 of FIG. 6A (like numerals indicate like parts); but the system 180 has an end sensor 182 which senses an end of the pipe 161 and produces an electronic signal which is transmitted by the end sensor to the PLC controller 173. In response to this signal, the PLC controller 173 can decouple the transducers from the pipe 161 (move the shoe away from and out of contact with the pipe 161). The system 180 also has a physical pipe stopper 184 which prevents further movement (to the right in FIG. 6C) of the pipe. When the pipe stops the shoe 172 is in a known position with respect to the end of the pipe 161. The PLC controller and/or the transducer system are interconnected with a computer or computers and/or monitors and/or display apparatus (e.g. as in FIG. 6E).

FIGS. 6E and 6F show a system 200 according to the present invention which, in some respects, is similar to the systems of FIGS. 6A and 6C (like numerals indicate like parts). A pipe 161 to be rotated and inspected is radially rotated by a rotation system 162 while a transducer system 171 for inspecting the pipe 161 is moved adjacent the pipe 161. A powered conveyor roller 216 (or rollers) move the pipe 161 axially (left and right in FIG. 6E) away from or toward a pipe stop 218. A water supply system 174 sprays water onto a shoe 172 of the transducer system 171 to provide water coupling between the shoe and the pipe to assist the transmission of ultrasonic signals to and away from the transducer system.

A water cleaning tray 222 receives excess water expelled by the shoe 172 for disposal or for recycling in the system. Optionally, the tray 222 is removable for cleaning dirt, debris, etc. accumulated therein. A compliant mount/suspension system 202 provides apparatus for raising and lowering the shoe 172 and a flexible support for the shoe 172 to accommodate irregularities and eccentricities in the pipe 161 as it is rotated adjacent the shoe 172. Any suitable known pipe rotation system may be used for the system 162. An optional pneumatic lift 204 raises the shoe 172 to contact the pipe 161 and lowers the shoe 172 to facilitate pipe loading or unloading. The lift 204 is controlled by the PLC controller 173. Hose and cable management apparatus 206 holds and accommodates various items—cables, wires, hoses, etc.—associated with the provision of water, electrical power, and signals to the various parts of the table 214 and parts of the system 200 (and such apparatus 206 may be used in the systems of FIGS. 6A and 6C). All mechanical functions of the system are controllable by the PLC controller.

A drive motor 208 mounted to the end of a ball/screw apparatus 212 moves the shoe 172 axially along the pipe 161. The ball/screw apparatus is part of a precision linear motion table 214 that accurately and precisely, and with stability, moves the transducer system 171 with respect to the pipe 161. The ball/screw apparatus 212 provides a linear drive for the movement of the shoe 172 along the pipe 161; and the encoder 210, attached to the ball/screw apparatus, provides location feedback information to the PLC controller 173. The PLC controller 173 and the ultrasonic transducers of the transducer system 171 provide data to a computer 220. The computer 220 is interconnected with either a monitor (or monitors) 221 and/or a strip chart recorder (or recorders) 223 to display inspection results. In one aspect inspection results are displayed to system operators in real-time. Also the computer 220 may, in certain aspects, be programmed to provide an alarm signal to a PLC controller to activate an alarm when a flaw is detected. There may be an alarm in or on the computer itself. Also, a known precision linear motion table may be used for the table 214.

An end sensor 182 senses the location of the shoe 172 with respect to the end of the pipe 161 and senses the location of the end of the pipe 161 when the transducer system 171 nears the pipe end (the end to the right in FIG. 6E).

Figure 7:
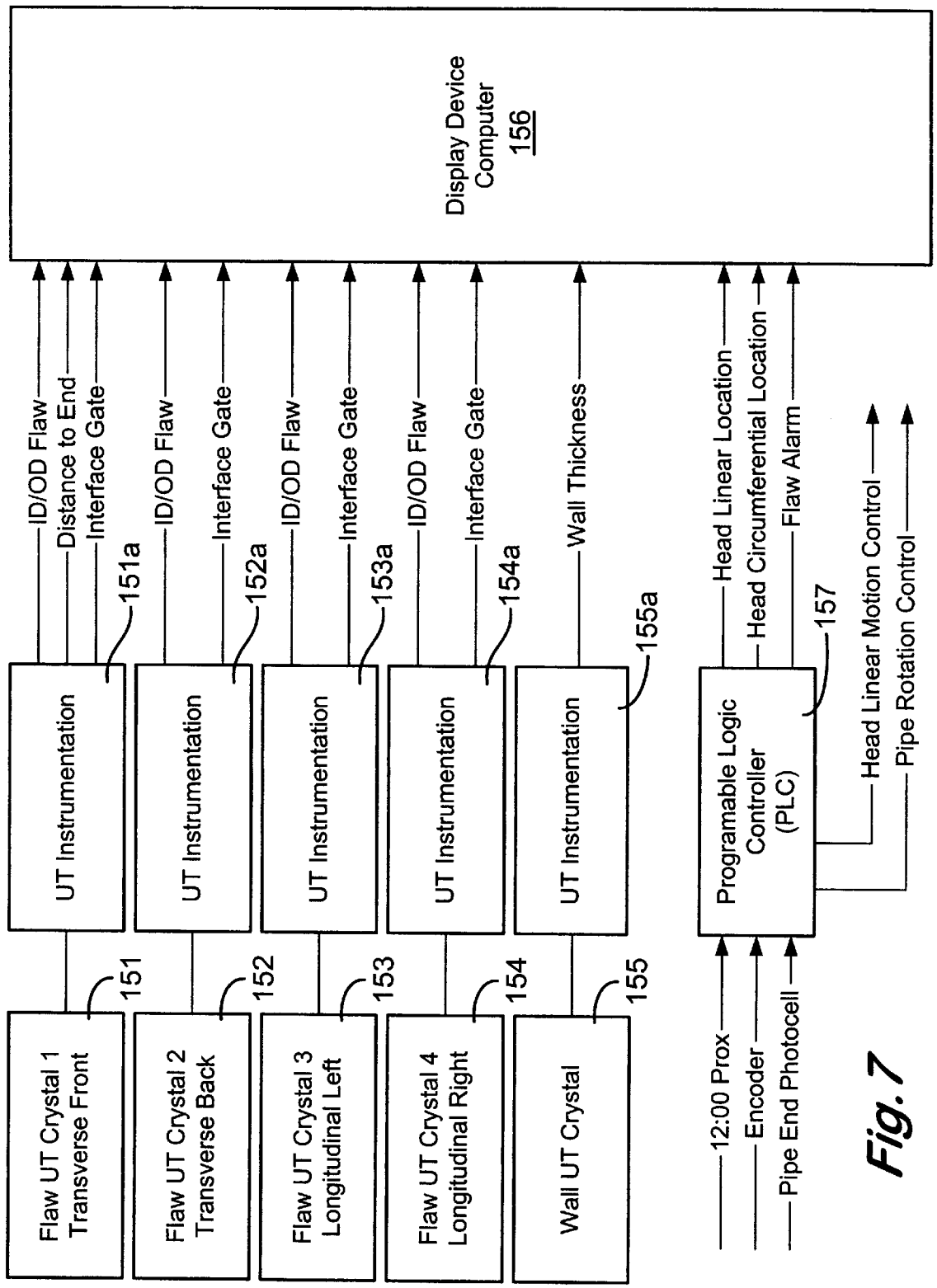
FIG. 7 is a schematic view of signal processing according to the present invention.

FIG. 7 illustrates schematically signal processing for an embodiment of a system and method according to the present invention for inspection signal transmission and use according to the present invention. In one aspect transducers 151–154 and 155—each with corresponding associated instrumentation 151a–154a correspond to the transducers 106 and 104, respectively, of the system 100 (FIG. 5A) or to the transducers 50a–50d and 52, respectively of the system 10 (FIG. 1A). The transducers 151–154 are for flaw detection and the transducer 155 is for measuring tubular member wall thickness. Ultrasonic electronic instrumentation is used which provides for the measurement of the amplitude of reflected sonic beams and the measurement of the time of flight of sonic beams to indicate, locate, and measure I.D. flaws, O.D. flaws, wall thickness, and time of flight to the end of a tubular member. The instrumentation also receives an interface signal that indicates the interface between a transducer and the tubular member as each firing sequence is initiated.

Each transducer is controlled by its associated instrumentation so that it transmits its sonic beam at specified time intervals at a specified repetition rate for a specified time duration, e.g., in some systems it may range between 50 milliseconds and a second. By imposing these electronic time data correction windows or "gates" ("Interface Gate") on the transducers' operation, the instrumentation permits the collection and processing of signal information only in the specified time windows. Thus if a flaw is indicated by a reflected signal, the location of the flaw is known. Each transducer can be used for both I.D. and O.D. flaw detection and for pipe end indication. A "Transverse Front" transducer faces the front of the tubular member (e.g., transducer 50a in FIG. 1A) and a "Transverse Back" transducer faces the back of the tubular member (e.g., transducer 50b in FIG. 1A). A "Longitudinal Left" transducer faces to the left (e.g., transducer 50c in FIG. 1A) and "Longitudinal Right" transducer faces to the right (e.g., transducer 50d in FIG. 1A).

A reflected beam is received back by a transducer following reflection from an end of the tubular or from a flaw at a surface; and the transducer then senses and receives an echo (reflected beam) which has an amplitude. If the echo is relatively small (i.e. with little or no amplitude), no flaw is indicated; if the echo has an amplitude that exceeds a pre-set value (programmed in the computer 156) then a flaw ("ID/OD Flaw") is indicated. Optionally the computer 156 produces a flaw alarm signal ("flaw alarm"; sound and/or visual). Flaw location and size are determined and are displayed by the computer 156. The transducer instrumentation for the transducer 155 produces a time of flight measurement (time of flight of a compressional wave packet from the interface, to the I.D. and back to the transducer) indicative of tubular wall thickness ("wall thickness") which is transmitted to the computer 156 (as digital information from the ultrasonic instrumentation) for wall thickness determination, alarm if necessary, and/or display.

When the transducer device nears the end of the pipe, a beam from the front transducer (e.g. 50a in FIG. 1A) reflects from the tubular end. Upon receipt of the beam reflected from the tubular end, the system calculates the distance from the front transducer to the end of the tubular (e.g. by using the time duration between an initial interface pulse and the time of the pulse reflected from the tubular end). The calculated distance-to-the-end of the tubular indicates if the transducer is at or near the end of the tubular member. When the front transducer has reached a position at which the system knows that the entire outer surface of the tubular has been inspected—a position near the tubular end at which part of the inner surface between the front transducer and the end of the tubular has not yet been inspected—the system continues with the inner surface inspection, ignoring any signal which may be received for time periods which would correspond to further outer surface inspection if the tubular end was not present; and while this inner surface inspection continues the system continuously detects and calculates the distance to the tubular end so that inner surface inspection is stopped when the front transducer's I.D. beam width reaches the tubular end. Due to the way in which the tubular member is rotated, the outer surface of the tubular member is completely examined—i.e., sonic beams are reflected from the entire outer surface—before the inner surface is completely examined. Therefore, the system, in certain aspects, ignores signals and their information related to any reflected beam other than those related to inner surface examination and end-reflected beams at a pre-set position of the transducer device.

The device 156 may include: a screen (or screens) (or strip chart apparatus) that displays a graphical representation of a tubular being examined, in one aspect in cross-section, with initial interface, end reflections, surface reflections, and flaw reflections; a computer (or computers) for analyzing the various signals from the transducers and/or from the PLC controller, e.g. to determine transducer location, tubular end location, wall thickness, defect existence, defect location, defect orientation and defect signal amplitude; and, if determined, for sending an alarm regarding insufficient wall thickness or defect indication; and for generating a report to or display for an operator which may be an interactive display to facilitate operational control of the system. Flaw location may be displayed in a two-dimensional display in which the horizontal axis is the tubular length and the vertical axis is the tubular's circumference; or flaw-reflected signal amplitude may be displayed as a function of tubular length on a strip chart. Display of the results of the tubular examination, and flaw display, may be done (with any system disclosed herein) in "real time" so that an operator sees (or is aware) of the detection of a defect as soon as the defect is detected.

Optionally, a computer of the system has a "GO/NO GO" capability with which it compares flaw signal amplitude to a preset threshold—based on an acceptable or unacceptable size flaw. The system then indicates whether the flaw renders the tubular acceptable or unacceptable. Similarly, the computer compares the amplitude of the wall thickness signal to a pre-set value to determine if the wall thickness is acceptable.

A programmable logic controller 157 ("PLC") (e.g. like that of the systems of FIGS. 6A, 6C, 6E) is interconnected electronically with: a computer; a motor like the motor of the systems of FIGS. 6A and 6C for moving the transducer system longitudinally with respect to a tubular to be inspected; the device 157 for providing information to the computer 156 regarding the location, both longitudinally ("Head Linear Location") and circumferentially ("Head Circumferential Location"), of the transducer system; a tubular rotation system ("Pipe Rotation Control") for controlling pipe rotation; an end sensor, like those of the systems of FIGS. 6A, 6C, and 6E, for receiving from the end sensor a signal indicative of transducer system location ("Pipe End Photocell") in reference to the tubular end; a mechanical and/or electronic and/or electromagnetic device or apparatus ("Encoder") that indicates location of the transducer system with respect to the end of the tubular; system for indicating each rotation of the tubular, e.g. a magnetic tubular sensing system or a light sensing system with a photocell that indicates each rotation of the tubular (e.g., in one aspect by sensing a reflective area on the tubular each time it rotates past a photocell, e.g. a reflector or reflective tape or paint at a 12 o'clock position on the tubular) ("12:00 Prox"). In one particular aspect the PLC controller 157 activates the motor that moves the transducer system ("head") in steps so that the end part of the tubular is examined (with the transducers stationary between steps and the tubular still rotating through 360 degrees for each step as described above). In other aspects the motor itself includes apparatus that activates the motor in steps (in one aspect commonly called a "Stepping Motor"), so that a full and complete inspection of a tubular is obtained, e.g. a shoe, for each rotation of the pipe, is indexed in steps or advanced in increments that are a fraction of the transducer beam width (e.g., but not limited to, $\frac{1}{32}$, $\frac{1}{16}$, $\frac{1}{8}$, $\frac{1}{4}$, $\frac{1}{2}$).

FIGS. 8A–8D illustrate the operation of an automated tubular inspection system according to the present invention (like any of the systems described herein) and show the end and near-end inspection of a tubular ("pipe") with an ultrasonic transducer system.

Figure 8A:
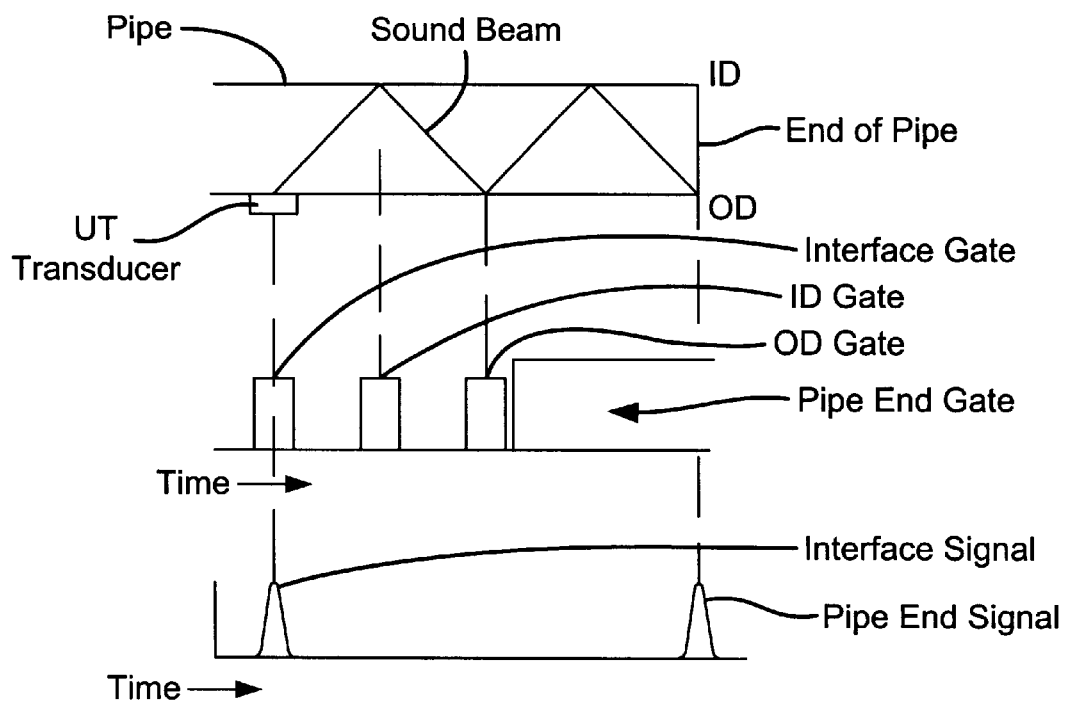
FIGS. 8A–8D schematically illustrate an inspection method according to the present invention.

As shown in FIG. 8A a front transducer ("UT TRANSDUCER") adjacent an outer surface ("OD") of a tubular member ("PIPE") at a specific time (horizontal axes are time axes) has fired an ultrasonic pulse ("SOUND BEAM") into the pipe a shear wave packet that has twice hit the pipe's inner surface ("ID"), once hit the pipe's outer surface, and has hit the end of the pipe at the outer surface ("END OF PIPE"). At this transducer location, the entire outer surface of the pipe has been examined (i.e., probed with a sonic beam); and a portion "a" of the pipe's inner surface has not yet been inspected. The sonic beam from the transducer follows the indicated path in both transmission and reflection. The transducer sends a sonic beam (a shear wave packet) directly across the pipe (upwards in FIG. 8A) which reflects back to the transducer from the pipe ID, producing the "INTERFACE SIGNAL" which indicates the transducer's location at the time of the sonic beam shown in FIG. 8A on the lowermost "TIME" axis. The reflection back from the end of the pipe produces "PIPE END SIGNAL" shown on the lowermost time axis. The time differential between the interface signal and the pipe end signal provides the basis for calculating the distance from the transducer to the end of the pipe. The computer using the speed of the sonic beam and the elapsed time between signals determines the distance to the pipe end. The transducer instrumentation is programmed with various time windows ("GATES") in which the transducer is activated to receive echoes from specific places; the "INTERFACE GATE" is a pre-set time window during which the transducer is operational for receiving the interface signal; the "ID GATE" is a pre-set time window pre-set for a specified time after the interface signal during which the transducer is operational for receiving an echo from the pipe ID of the sonic beam's first hit on the pipe ID following transmission of the sonic beam from the transducer; the "OD GATE" is a pre-set time window pre-set for a specified time after the interface signal during which the transducer is operational for receiving an echo from the sonic beam's first hit on the pipe OD; and the "PIPE END GATE" is a pre-set time window during which the transducer is operational for receiving an echo from the pie end.

As shown in FIG. 8A, the sonic beam has encountered no tubular defect at either pipe surface and no defect signal is indicated on lowermost time axis. Any defect within the ID GATE or OD GATE would have resulted in the production of a signal with an amplitude above that of the lowermost time axis.

The temporal duration of the three gates shown in FIG. 8A is based on the velocity of sound through the material of the particular tubular member and its wall thickness. Once they are determined, these gates are set (by an operator) in the transducer instrumentation.

Figure 8B:
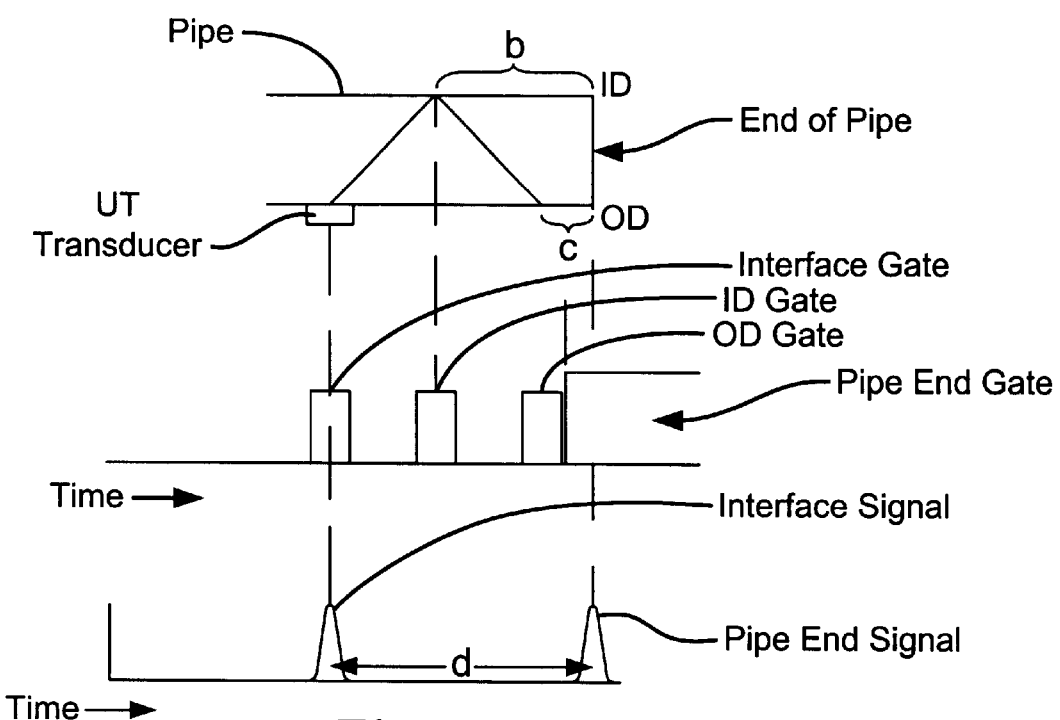

As shown in FIG. 8B the transducer has moved closer to the pipe end; except for the length "b", the pipe's inner surface has been inspected; except for the length "c" (which is less than the length "b") the pipe's outer surface has been inspected; and no defect has been detected. The PIPE END SIGNAL indicates that the transducer is a distance "d" from the pipe end.

Figure 8C:
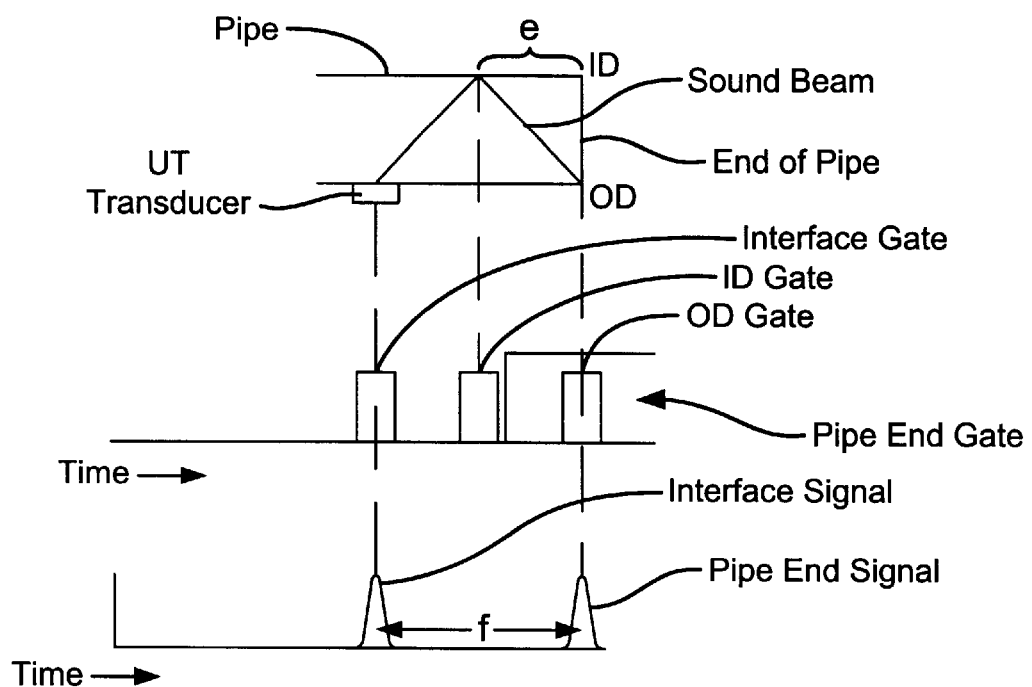

As shown in FIG. 8C, the entire pipe outer surface has been examined; a length "e" of the pipe's inner surface has not yet been examined; and the transducer is a distance "f" from the pipe end. Signals from the O.D. gate are not originated by an O.D. flaw and are, therefore ignored; i.e., the system is now programmed to look for the pipe end in the pipe end gate and to ignore as an indication of an O.D. flaw and signals from the O.D. gate since the O.D. examination has been completed—there is no more pipe outer surface to be examined, no more pipe outer surface past (to the right in FIG. 8C) the pipe end.

Figure 8D:
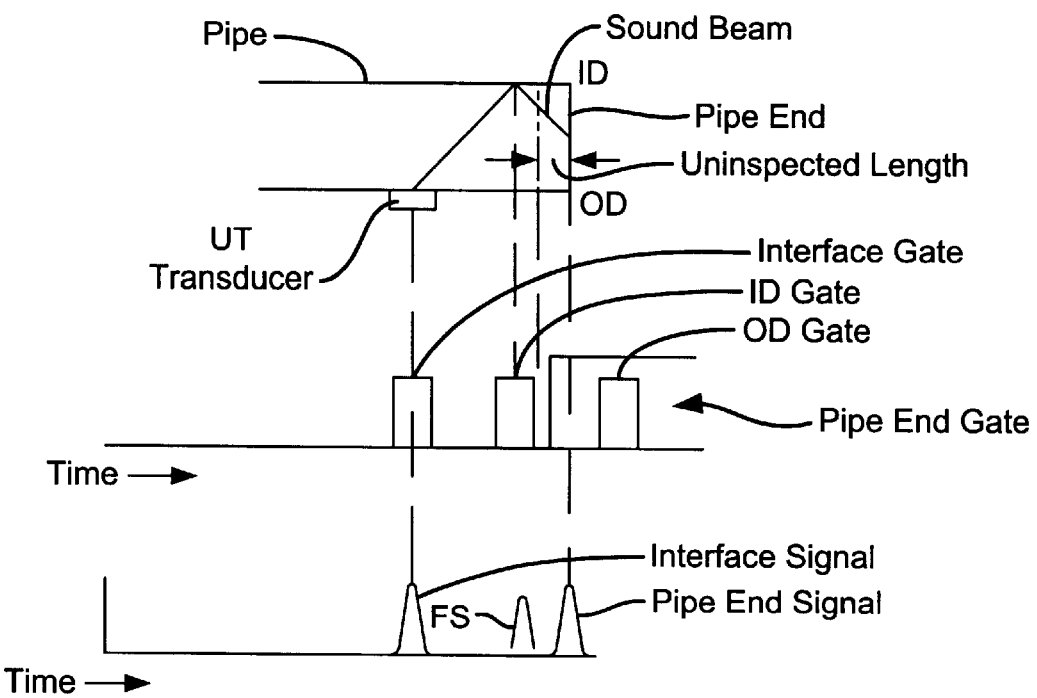

As shown in FIG. 8D, once the entire outer surface has been inspected (shown in FIG. 8C) the transducer continues to move toward the pipe end transmitting the sonic beam to inspect the remaining portion (length "e") of the inner surface while continuously receiving the end signal that indicates that the transducer is getting closer and closer to the pipe end. Thus, the inspection of the entire inner surface is completed; at which point the pipe end signal indicates that the transducer is at the end of the pipe and the system moves the transducer system away from the pipe (decouples it).

In order to accurately ascertain the distance to the end of the pipe, to finish and complete the pipe I.D. inspection, and to insure that the pipe end is sensed when the transducer moves to a point adjacent the pipe end, the PIPE END GATE is moved so that it begins immediately after the completion of the ID GATE. The movement of the shoe with the transducers is halted when the inspection has been completed.

The "UNINSPECTED LENGTH" in FIG. 8D indicates the length of the I.D. that has not yet been inspected due to the limitations of distinguishing a relatively small flaw signal from a relatively large end signal.

For illustrative purposes a flaw signal FS is shown on FIG. 8D whose amplitude (height in FIG. 8D above the lower most time axis) is less than the amplitude of the INTERFACE SIGNAL and less than the amplitude of the PIPE END SIGNAL. The amplitude of the flaw signal FS can provide a defect indication which indicates that a defect of such extent is present that the pipe may be rejectable; i.e. the amplitude exceeds a threshold amplitude (an amplitude initially calibrated for flaws from a fixed known reference flaw). In one aspect this threshold amplitude is the height of the I.D. gate. The system provides an alarm as discussed above when there is a defect indication and/or optionally provides a "NO GO" indication for the rejection of the tubular being examined.

The present invention, therefore, provides in certain, but not necessarily all embodiments, a method for ultrasonically inspecting a tubular member, the tubular member having an inner surface, an outer surface, and two spaced-apart ends including a first end of the tubular member, the method including transmitting sonic beams to the tubular member with one or more transducers such that sonic beams are reflected from: the inner surface of the tubular member, the outer surface of the tubular member, and from the first end of the tubular member; completing and/or ceasing inspection of the outer surface of the tubular member for outer surface defects while continuing to inspect the inner surface of the tubular member for inner surface defects; while continuing to inspect the inner surface of the tubular member for inner surface defects after ceasing outer surface inspection, sensing a distance from the transducer(s) to the first end of the tubular member, and, the transducer(s) continuing to transmit sonic beams for the inspection of the inner surface of the tubular member until the transducer(s) are near the first end of the tubular member.

Such a method may also include one, some (in any possible combination) or all of the following: wherein the tubular member has an inner surface defect near the first end of the tubular member and the method including transmitting a sonic beam from the transducer(s) such that the sonic beam is reflected from the inner surface defect, receiving the reflected beam from the inner surface defect of the tubular member, producing a defect signal related to the sonic beam reflected from the inner surface defect, the defect signal for conveying information about the inner surface defect, and transmitting the defect signal to signal analysis apparatus to analyze and indicate the inner surface defect; producing an end signal related to a beam reflected from the first end of the tubular, the end signal having information, e.g. in digital form, about the first end of the tubular member, calculating an end distance from the transducer(s) to the first end of the tubular member using the information of the end signal, and until the end distance is less than a first pre-set value continuing to inspect the surfaces of the tubular member; until the end distance is less than a second pre-set value, continuing to inspect the outer surface of the tubular member; when the end distance is less than the second pre-set value, continuing to inspect the inner surface of the tubular member; when the end distance is less than the first pre-set value, ceasing inspection of the inner surface of the tubular member; wherein the first pre-set value is one-eighth of an inch; wherein the first pre-set value is two or three millimeters; wherein the inner surface defect is within two or three millimeters of the first end of the tubular; wherein the inner surface defect is within one-eighth of an inch of the first end of the tubular; wherein substantially all of the surface of the tubular member is accurately inspected for inner surface defects; wherein each transducer has associated instrumentation for controlling each transducer; wherein a programmable logic controller controls movement means that moves the tubular member during inspection of the tubular member and that moves the transducer(s) with respect to the tubular member; wherein a computer or computers analyze signal information and associated display apparatus displays inspection results; providing relative helical motion between the tubular member and the transducer(s) to trace a helical path around the surfaces of the tubular member with the sonic beams; transmitting sonic beams longitudinally and transversely through the member with transducers; wherein the sonic beams are transmitted longitudinally, transversely, and obliquely into the tubular member; wherein the transducer(s) are mounted on a waveguide support having a single beam passage area and the reflected beams bass through the single beam passage area; tracking a position of the transducer(s) and producing a location signal indicative of said position(s); stopping relative motion between the tubular member and the transducer(s) when said location signal indicates that the transducer(s) are within a pre-set distance to an end of the tubular member; wherein movement of the tubular member is stopped by stopper apparatus; wherein an end of the tubular member is sensed with end sensor apparatus and the end sensor apparatus sends an end signal to a control system that controls movement of the transducer(s), receipt of the end signal by the control system, and stopping movement of the transducer(s) by the control system in response to the end signal; moving the transducer(s) in indexed step increments; wherein each indexed step increment of the indexed step increments is a fraction of a beam width of a sonic beam from the transducer(s); and/or wherein the fraction is from the group consisting of ⅟32, ⅟16, ⅛, ¼, and ½.

The present invention, therefore, provides in certain, but not necessarily all embodiments, a method for ultrasonically inspecting a tubular member, the method including transmitting sonic beams through the tubular member with at least one transducer so that sonic beams are reflected from an inner surface of the tubular member, from an outer surface of the tubular member, and from defects of the tubular member, if any; and receiving with the at least one transducer reflected beams from the surface defects of the tubular member, if any, from the inner surface and from the outer surface of the tubular member; sensing an end distance from the at least one transducer to an end of the tubular member, and ceasing inspection (either O.D., I.D., or both) of the tubular member when the end distance is less than a pre-set value.

The present invention, therefore, provides in certain, but not necessarily all embodiments, an ultrasonic inspection device useful for inspecting a tubular member having one or more transducers for transmitting sonic beams and for receiving reflected beams thereof from inner and outer surfaces of the tubular member, from ends of the tubular member including a first end spaced apart from a second end, and from defects of the tubular member, the reflected beams including beams reflected from an outer surface of the tubular member, from an inner surface of the tubular member, from the first end of the tubular member, and from an inner surface defect of the tubular member, and means for differentiating the reflected beams, means for producing signals corresponding to information about the reflected beams, including a defect signal having information about the inner surface defect, and an end signal having information about the end of the tubular member, and means for continuing inspection of the inner surface of the tubular member for inner surface defects (in one aspect after ceasing to inspect the O.D.) until the end distance is less than a pre-set value. Such a method may also include one, some (in any possible combination) or all of the following: means for ceasing inspection of the outer surface of the tubular member when all but about one-eighth of an inch of the tubular member's length has been inspected; means for providing relative helical motion between the tubular member and the transducer(s) to trace a helical path with sonic beams around the tubular member; means for indicating position of the transducer(s) with respect to an end of the tubular member; the means for indicating the position of the transducer(s) including encoder apparatus; the means for indicating the position of the transducer(s) including end sensor apparatus; means for energizing and de-energizing the transducer(s) to sequentially transmit and receive sonic beams; an array of opposing transducers for transmitting sonic beams, and transducer positioning means to which the transducer(s) are connected for positioning the transducer(s) to transmit the sonic beams longitudinally, transversely, and obliquely through the tubular member such that beams are reflected from parts of the tubular member; a wall thickness transducer for measuring time of sonic beam flight to determine tubular member wall thickness; waveguide support apparatus supporting the transducer(s) and having a single beam passage area through which all transmitted and reflected beams pass; and/or means for moving the transducer(s) in indexed steps with respect to the tubular member.

The present invention, therefore, provides in certain, but not necessarily all embodiments, a waveguide support for an ultrasonic inspection device useful for inspecting tubular members, the waveguide support for supporting one or a plurality of ultrasonic transducers, the waveguide support including a body of waveguide material, the body having a single beam passage area through which sonic beams from all of the ultrasonic transducer(s) are passable and back through which all sonic beams reflected from the tubular member are passable back to the transducers. Such a method may also include one, some (in any possible combination) or all of the following: a plurality of transducers on the body for transmitting sonic beams and for receiving reflected beams thereof from the tubular member; at least one transducer having a sensitive crystal area and the single beam passage area slightly larger than the sensitive crystal area; and/or wherein the at least one transducer is a plurality of transducers each with a sensitive crystal area of substantially the same area.

The present invention, therefore, provides in certain, but not necessarily all embodiments, a method for ultrasonically inspecting a weld on a tubular member, the method including transmitting sonic beams from one or more ultrasonic transducers to inspect the weld, receiving reflected beams from the weld, and moving the ultrasonic transducers adjacent the weld in step-wise manner; such a method wherein each transducer has associated instrumentation for controlling each transducer, and wherein a programmable logic controller controls movement means that rotates the tubular member with respect to the ultrasonic transducer(s) and wherein movement means moves the transducer(s) with respect to the tubular member; and/or means for providing relative helical motion between the tubular member and the transducer(s) to trace a helical path of sonic beams from the ultrasonic transducer(s) around the tubular member, and means for indicating position of the transducer(s) with respect to an end of the tubular member.

FIG. 9A shows a system 250 according to the present invention which is like other systems according to the present invention described herein, e.g. like the systems of FIGS. 6A, 6E and 8A, and parts like those of the system of FIG. 6A have like numerals. However, the system 250 has one or two proximity switches 251, 252 (or photocell sensor apparatuses) which are activated by passage of a UT transducer system 271 [and its accompanying instrumentation 253 (like instrumentation 151a–155a, FIG. 7] for providing ID and OD flaw inspection (like, e.g., the transducer system 171, FIG. 6A) near the proximity switches. Alternatively, rod, beam or other suitable member 255 (see FIGS. 10A, 10B) connected to the UT transducer system 271 is located so that the rod 255 moves adjacent the proximity switch(es), thereby activating it or them so that it or they send a signal to the PLC controller 173 to stop inspection of the OD or ID, respectively, of a pipe 161 being inspected. It is to be understood that other components of a system according to the present invention like that described above (e.g. FIGS.

6A–7) are present for the system 250 (e.g., but not limited to pipe rotation apparatus, like the system 162, FIG. 6A; sensing system, like the system 170, FIG. 6A; water supply system, like the system 174, FIG. 6A; transducer instrumentation apparatus; shoe and shoe movement system, like the shoe 172 and system 176, FIG. 6A; mount and precision linear motion table, like the mount 177 and table 178, FIG. 6A; etc); but the computer 156 is deleted and no sensing of the distance to the end of the pipe is done (since the "ID PROX" proximity switch signals when the UT transducer is at a point at which ID inspection can cease. Alternatively a drive motor/drive shaft apparatus may be used to move the UT transducer system.

Figure 10A:
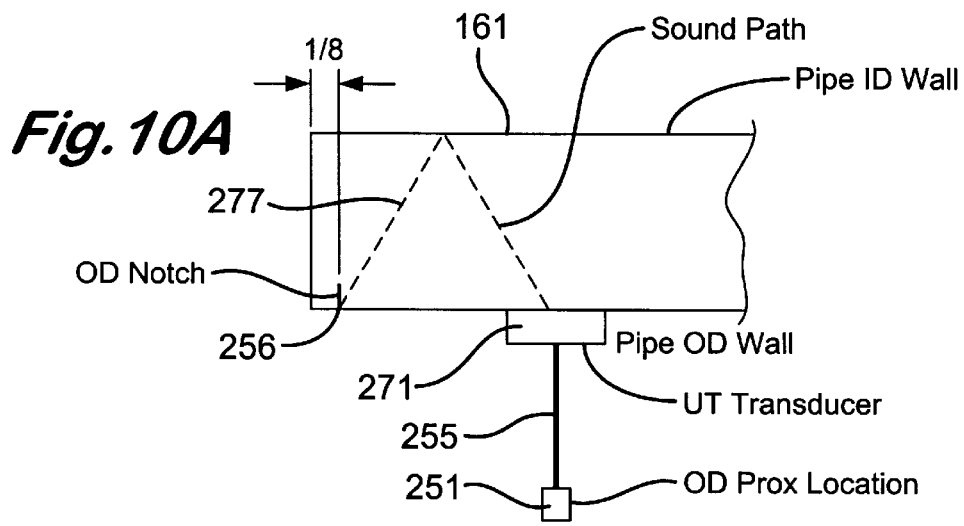
FIGS. 10A, 10B, and 10C are schematic views of systems according to the present invention.

As shown in FIG. 9B, the location of the UT transducer 271 is controlled by the PLC controller 173. Any desired number of UT transducers may be used (e.g., but not limited to, ten tarnsducers on a waveguide or shoe). Upon receipt of a signal from the OD proximity switch 251 that it has sensed the UT transducer 271 (or a rod 255 extending therefrom as illustrated in FIG. 10A), the PLC controller ignores OD signals from the UT Instrumentation 253 and thus inspection of the OD of the pipe 161 ceases (e.g. within a preset distance of the pipe end, e.g. within one-eighth or one sixteenth inch of an end of the pipe—and the system, as any herein, can inspect up to such a distance with respect to both ends of a pipe). The OD proximity switch 251 is located at a position corresponding to a location past which the UT transducer 271 would inspect an end portion of the pipe 161, e.g., as shown, the last ⅛ inch of the pipe, although in other embodiments according to the present invention the OD proximity switch may be located any desired distance from the pipe end, including, but not limited to, ¼ inch or 1/16 inch. This location can take into account the "footprint" or width of the ultrasonic beam being used. An OD flaw signal from the UT instrumentation will be ignored by the PLC controller 173 once the OD proximity switch 251 has sent its signal (or in other aspects in which an ID proximity switch is first encountered, an ID flaw signal will be ignored by the PLC controller). A pipe stopper 284 physically stopd the pipe.

Figure 10B:
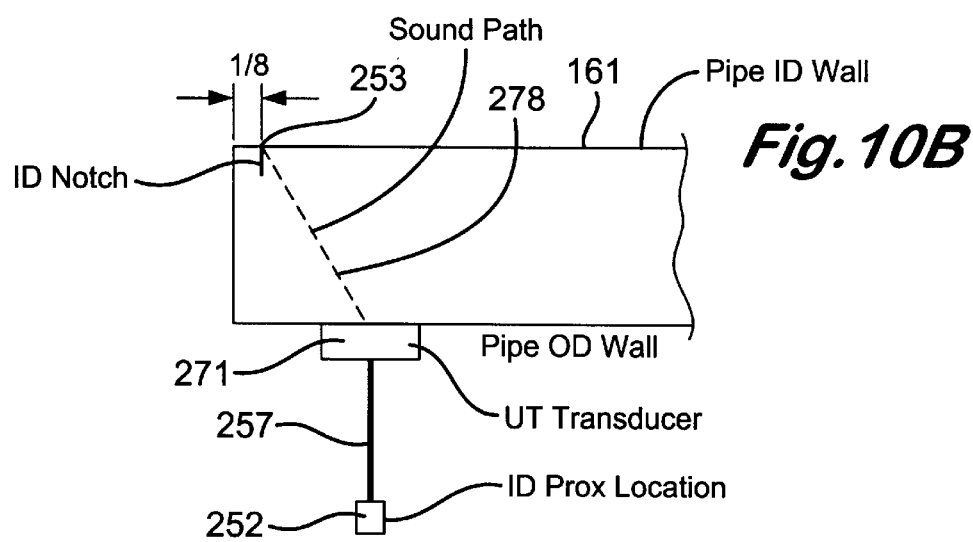

After the OD inspection ceases, ID inspection continues until, as shown in FIG. 10B, the rod 257 moves adjacent the ID proximity switch 252 at which point it sends a signal to the PLC controller 173. The PLC controller 173 then ignores further ID signals from the UT Instrumentation upon movement of the UT transducer 271 back to an initial position adjacent a "START" proximity switch 258. The PLC is signalled so that it knows that the UT transducer 271 is again in position to start an inspection.

Optionally, an alarm (audio and/or visual) may be interconnected with the PLC controller for activation upon receipt of a flaw signal (provided that the proximity switch has not been encountered). As shown in FIG. 9B an audio alarm 259 provides a sound alarm upon receipt of a flaw signal. "START PROX" in FIGS. 9A and 9B indicate a proximity switch (or photocell) at the beginning of the travel of the UT transducer 271. If an OD or an ID flaw is detected by the system 250 between the starting proximity sensor ("START PROX") and the OD proximity switch 251 and ID or OD alarm signal is sent to the PLC controller 173 and a corresponding alarm signal is sent from the PLC controller to the alarm 259 and an audio alarm is sounded (or alternatively a flashing light is used). If an ID flaw in the pipe 161 is sensed between the OD proximity sensor and the ID proximity sensor, an ID alarm signal is sent by the UT instrumentation 253 to the PLC controller 173 and an ID flaw alarm is generated. Any system according to the present invention may employ an ID proximity switch, an OD proximity switch, or both, with or without corresponding rods 255, 257. Any alarm herein may also indicate and differentiate between an ID flaw and an OD flaw.

As shown in FIG. 10A, the OD proximity switch 251 can be located so that an ultrasonic pulse 277 from the UT transducer 271 is reflected from the ID wall of the pipe 161 and then hits an OD notch 256 which is a desired distance from the end of the pipe (e.g. ⅛" as shown, or, preferably, between ¼" and 1/16"). The OD notch 256 is made in the pipe prior to inspection. Similarly, as shown in FIG. 10B, the ID proximity switch 252 can be located with respect to an ID notch 253 so that an ultrasonic pulse 278 from the UT transducer 271 hits an ID notch 253 (made in the pipe prior to inspection and located a desired known distance from the pipe end—as shown, ⅛"). Thus the ID and OD notches are, in effect, detectable artificial flaws positioned in a known location.

Figure 10C:
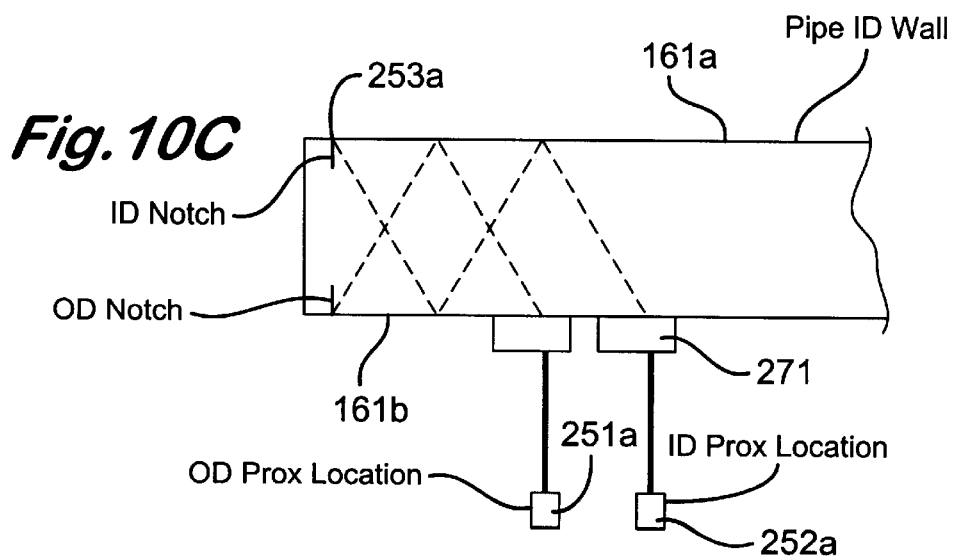

As shown in FIGS. 10A and 10B, for OD notch detection the ultrasonic pulse is reflected once (FIG. 10A) from the pipe ID wall before it contacts the OD notch (the pulse has two "legs") and the ultrasonic pulse is not reflected (FIG. 10B) from the pipe wall before it hits the ID notch (the pulse has one "leg"); but, it is within the scope of the present invention (for any system and method disclosed herein) to use a multi-legged pulse (e.g. three, five, or more legs) for contacting the ID notch and a multi-legged pulse (e.g., two, four, six or more legs) for contacting the OD notch. The location of the ID notch and/or OD notch is adjusted depending on the number of reflections (legs) used and thus the ID proximity switch and/or OD proximity switch will have a corresponding location with respect to the pipe end (a location corresponding to the location of the UT transducer when it emits the known multi-leg pulse). It should also be noted that, according to the present invention, it is, therefore, possible to have the UT transducer first encounter an ID proximity switch prior to encountering an OD proximity switch. For example, as shown in FIG. 10C, the UT transducer encounters an ID proximity switch 252a prior to encountering an OD proximity switch 251a—and the ultrasonic pulse from the UT transducer 271 that contacts the ID notch 253a and which is reflected once from the pipe ID wall 161a and once from the pipe OD wall 161b (i.e., the pulse has three "llegs"). As shown in FIG. 10C the ultrasonic pulse from the UT transducer when it is adjacent the OD proximity switch 251a will have two legs, but, as described above, a multi-legged pulse of four or more legs may be used for OD notch detection with the OD proximity switch located appropriately. It is within the scope of the present invention to use such multi-legged pulses for any system according to the present invention, including, but not limited to, those referred to with respect to FIGS. 6A, 6E, 7, 8A, and 9A.

Figure 11:
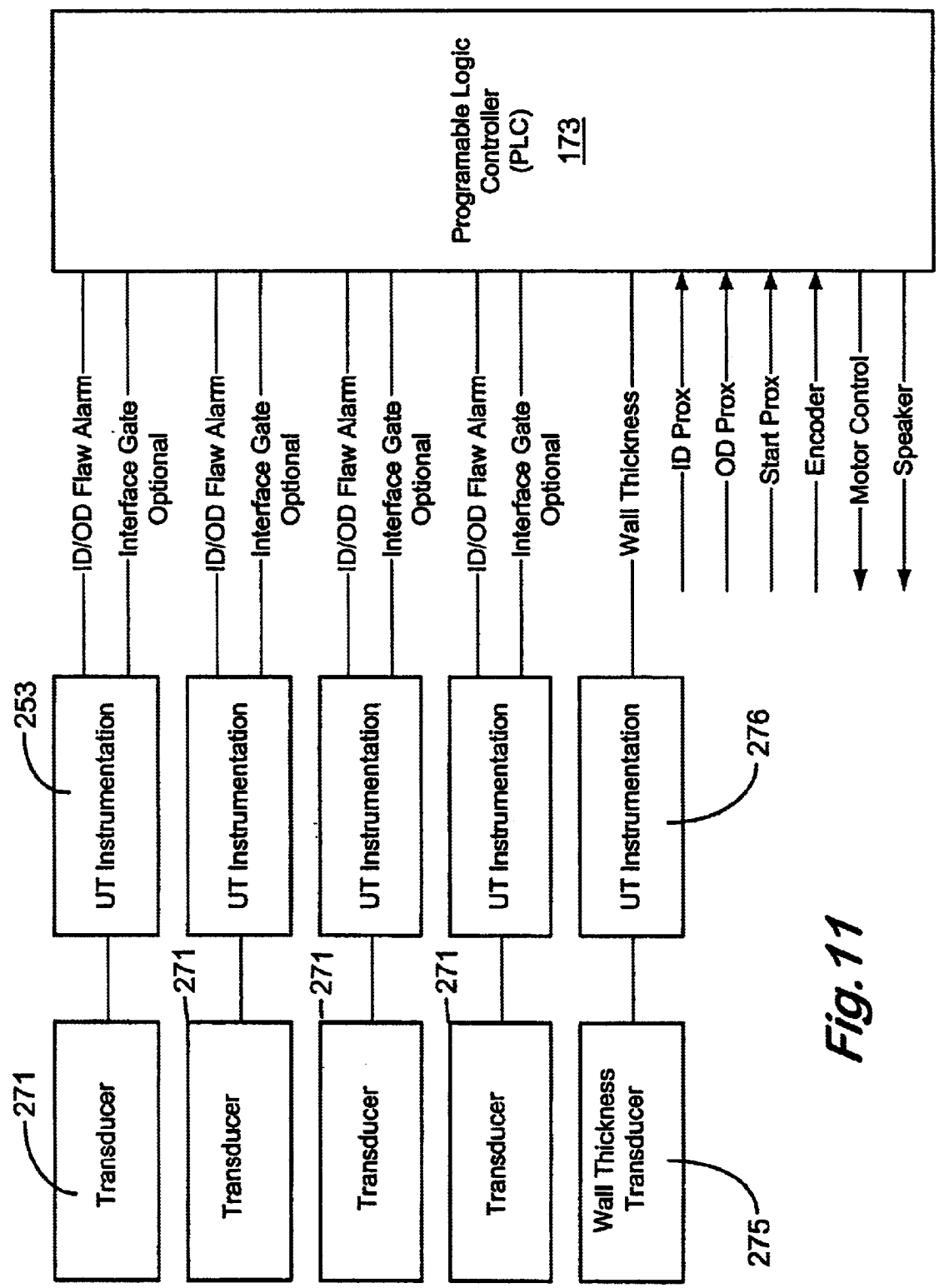
FIG. 11 is a schematic view of signal processing according to the present invention.

FIG. 11 shows schematically an instrumentation/control diagram for a system like the system 250 according to the present invention like that of FIG. 9A which has no computer 156 (like that in FIG. 7) and in which no signal related to distance-to-end-of-pipe is sent by a UT transducer to a PLC controller. The system shown in FIG. 11 has four transducers 271 (the top four) and a wall thickness transducer 275 each with corresponding instrumentation 253, 276, respectively. It is within the scope of this invention to use any suitable known logic control signal processing device for the PLC controller.

The present invention provides, therefore, in some but not necesssarily all embodiments, a method for ultrasonically inspecting a tubular member, the tubular member having a first surface, a second surface, the first surface spaced apart from the second surface by a thickness of the tubular member, and two spaced-apart ends including a first end of the tubular member, the method including transmitting sonic beams to the tubular member with transducer apparatus such that sonic beams are reflected from the first surface of the tubular member and from the second surface of the tubular member, the transducer apparatus controlled by control apparatus, while continuing to inspect the first surface of the tubular member for first surface defects, moving the transducer apparatus adjacent sensing apparatus which signals the control apparatus to cease processing of transducer apparatus signals related to inspection of the second surface, and, the transducer apparatus continuing to transmit sonic beams for the inspection of the first surface of the tubular member, and completing inspection of substantially all of the second surface of the tubular member for second surface defects while continuing to inspect the first surface of the tubular member for first surface defects. Such a method may include one or some, in any possible combination, of the following: wherein the first surface is a surface of an inner wall of the tubular member and the second surface is a surface of an outer wall of the tubular member, or vice-versa; wherein the control apparatus comprises a logic control signal processing device; wherein the sensing apparatus is a second proximity switch activatable by the presence of the transducer apparatus adjacent said proximity switch; wherein the sensing apparatus includes a first proximity switch for signalling the control apparatus to cease processing of transducer apparatus signals related to inspection of the first surface, the method further including completing inspection of substantially all of the first surface of the tubular member for first surface defects; wherein completion of inspection of substantially all of the tubular member for both first surface defects and second surface defects includes inspecting the tubular member's length up to a distance between one four and one sixteenth inches from the first end, with the first and second proximity switches correspondingly positioned for said inspection completion; wherein the tubular member has a surface and the method further including transmitting a sonic beam from the transducer apparatus such that the sonic beam is reflected from the inner surface defect, receiving the reflected beam from the surface defect, producing a defect signal related to the sonic beam reflected from the surface defect, the defect signal for conveying information about the surface defect, and transmitting the defect signal to signal analysis apparatus to analyze and indicate the surface defect; wherein the surface defect is a first surface defect; wherein the surface defect is a second surface defect; wherein substantially all of the entire surface of the tubular member is accurately inspected for surface defects; wherein the transducer apparatus has associated instrumentation for the transducer apparatus wherein a programmable logic controller controls movement apparatus that moves the tubular member during inspection of the tubular member and that moves the transducer apparatus with respect to the tubular member; wherein associated display apparatus displays inspection results; providing relative helical motion between the tubular member and the transducer apparatus to trace a helical path around the surfaces of the tubular member with the sonic beams; transmitting sonic beams longitudinally and transversely through the member with the transducer apparatus; wherein the sonic beams are transmitted longitudinally, transversely, and obliquely into the tubular member; wherein the transducer apparatus is mounted on a waveguide support having a single beam passage area and the reflected beams bass through the single beam passage area; tracking a position of the transducers and/or producing a location signal indicative of said position; stopping relative motion of the tubular member with a pipe stopper; wherein the transducer apparatus includes multiple ultrasonic transducers; moving the transducer apparatus in indexed step increments; and/or wherein each indexed step increment of the indexed step increments is a fraction of a beam width of a sonic beam from the transducers.

The present invention provides, therefore, in at least certain embodiments, an ultrasonic inspection device useful for inspecting a tubular member having transducer apparatus for transmitting sonic beams and for receiving reflected beams thereof from inner and outer surfaces of the tubular member, and from defects of the tubular member, the reflected beams including beams reflected from an outer surface of the tubular member and from an inner surface of the tubular member, and from a defect of the tubular member, and apparatus for differentiating the reflected beams, apparatus for producing signals corresponding to information about the reflected beams, including a defect signal having information about the defect, and an end signal from proximity switch apparatus positioned with respect to an end of the tubular member, and apparatus for continuing inspection of one surface of the tubular member following cessation of inspection of the other surface of the tubular member; and such an ultrasonic inspection device with apparatus for ceasing inspection of the tubular member when all but about one-eighth of an inch at one end or at both ends of the tubular member's length has been inspected.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form it may be utilized. The invention claimed herein is new and novel in accordance with 35 U.S.C. §102 and satisfies the conditions for patentability in §102. The invention claimed herein is not obvious in accordance with 35 U.S.C. §103 and satisfies the conditions for patentability in §103. This specification and the claims that follow are in accordance with all of the requirements of 35 U.S.C. §112. The inventors may rely on the Doctrine of Equivalents to determine and assess the scope of their invention and of the claims that follow as they may pertain to apparatus not materially departing from, but outside of, the literal scope of the invention as set forth in the following claims.

What is claimed is:

1. A method for ultrasonically inspecting a tubular member, the tubular member having a first surface and a second surface, the first surface spaced apart from the second surface by a thickness of the tubular member, and two spaced-apart ends including a first end and a second end of the tubular member, the method comprising transmitting sonic beams to the tubular member with transducer apparatus such that sonic beams are reflected from the first surface of the tubular member and from the second surface of the tubular member, the transducer apparatus controlled by control apparatus, while continuing to inspect the first surface of the tubular member for first surface defects, moving the transducer apparatus adjacent sensing apparatus which signals the control apparatus to cease processing of transducer apparatus signals related to inspection of the second surface, and, the transducer apparatus continuing to transmit sonic beams for the inspection of the first surface of the tubular member, and completing inspection of substantially all of the second surface of the tubular member for second surface defects while continuing to inspect the first surface of the tubular member for first surface defects.

2. The method of claim 1 wherein the first surface is a surface of an inner wall of the tubular member and the second surface is a surface of an outer wall of the tubular member.

3. The method of claim 1 wherein the first surface is a surface of an outer wall of the tubular member and the second surface is a surface of an inner wall of the tubular member.

4. The method of claim 1 wherein the control apparatus comprises a logic control signal processing device.

5. The method of claim 1 wherein the sensing apparatus is a second proximity switch activatable by the presence of the transducer apparatus adjacent said proximity switch.

6. The method of claim 5 wherein the sensing apparatus includes a first proximity switch for signalling the control apparatus to cease processing of transducer apparatus signals related to inspection of the first surface, the method further comprising completing inspection of substantially all of the first surface of the tubular member for first surface defects.

7. The method of claim 6 wherein completion of inspection of substantially all of the tubular member for both first surface defects and second surface defects includes inspecting the tubular member's length up to a distance between one four and one sixteenth inches from each end of the tubular member, with the first and second proximity switches correspondingly positioned for said inspection completion.

8. The method of claim 5 wherein either the first surface or the second surface of the tubular member is an inner surface of the tubular member and the method further comprising transmitting a sonic beam from the transducer apparatus such that the sonic beam is reflected from an inner surface defect receiving the reflected beam from the inner surface defect, producing a defect signal related to the sonic beam reflected from the inner surface defect, the defect signal for conveying information about the inner surface defect, and transmitting the defect signal to signal analysis apparatus to analyze and indicate the inner surface defect.

9. The method of claim 8 wherein the surface defect is a first surface defect.

10. The method of claim 8 wherein the inner surface defect is a second surface defect.

11. The method of claim 1 wherein means are provided for producing an alarm when a surface defect is detected, the method further comprising providing an alarm when a surface defect is detected.

12. The method of claim 1 wherein the transducer apparatus has associated instrumentation for the transducer apparatus.

13. The method of claim 1 wherein a programmable logic controller controls movement means that moves the tubular member during inspection of the tubular member and that moves the transducer apparatus with respect to the tubular member.

14. The method of claim 13 wherein associated display apparatus displays inspection results.

15. The method of claim 1 further comprising providing relative helical motion between the tubular member and the transducer apparatus to trace a helical path around the surfaces of the tubular member with the sonic beams.

16. The method of claim 1 further comprising transmitting sonic beams longitudinally and transversely through the member with the transducer apparatus.

17. The method of claim 1 wherein the sonic beams are transmitted longitudinally, transversely, and obliquely into the tubular member.

18. The method device of claim 1 wherein the transducer apparatus is mounted on a waveguide support having a single beam passage area and the reflected beams bass through the single beam passage area.

19. The method of claim 1 further comprising the steps of tracking a position of the transducer apparatus and producing a location signal indicative of said position.

20. The method of claim 1 further comprising the steps of providing relative motion of the tubular member and stopping relative motion of the tubular member with a pipe stopper.

21. The method of claim 1 wherein the transducer apparatus includes multiple ultrasonic transducers.

22. The method of claim 1 further comprising moving the transducer apparatus in indexed step increments.

23. The method of claim 22 wherein each indexed step increment of the Indexed step increments is a fraction of a beam width of a sonic beam from the transducer apparatus.

24. An ultrasonic inspection device useful for inspecting a tubular member comprising transducer apparatus for transmitting sonic beams and for receiving reflected beams thereof from inner and outer surfaces of the tubular member, and from defects of the tubular member, the reflected beams including beams reflected from an outer surface of the tubular member and from an inner surface of the tubular member, and from a defect of the tubular member, and means for differentiating the reflected beams, means for producing signals corresponding to information about the reflected beams, including a defect signal having information about the defect, and an end signal from proximity switch apparatus positioned with respect to an end of the tubular member, and means for continuing inspection of one surface of the tubular member following cessation of inspection of the other surface of the tubular member.

25. The ultrasonic inspection device of claim 24 further comprising means for ceasing inspection of the tubular member when all but about one-eighth of an inch at one end of the tubular member's length has been inspected.

* * * * *